US012770737B2

(12) United States Patent
Kourtis et al.

(10) Patent No.: US 12,770,737 B2
(45) Date of Patent: Oct. 20, 2026

(54) PHYSIOLOGICAL DATA MONITORING SYSTEM

(71) Applicant: Eli Lilly and Company, Indianapolis, IN (US)

(72) Inventors: Iraklis Kourtis, Arlington, MA (US); Lampros Kourtis, Cambridge, MA (US); Brian Ellis Winger, Indianapolis, IN (US); Jian Yang, Newton, MA (US)

(73) Assignee: Eli Lilly and Company, Indianapolis, IN (US)

( * ) Notice: Subject to any disclaimer, the term of this patent is extended or adjusted under 35 U.S.C. 154(b) by 453 days.

(21) Appl. No.: 18/006,593

(22) PCT Filed: Aug. 18, 2021

(86) PCT No.: PCT/US2021/046497

§ 371 (c)(1),
(2) Date: Jan. 24, 2023

(87) PCT Pub. No.: WO2022/040307

PCT Pub. Date: Feb. 24, 2022

(65) Prior Publication Data

US 2023/0274833 A1 Aug. 31, 2023

Related U.S. Application Data

(60) Provisional application No. 63/070,889, filed on Aug. 27, 2020.

(30) Foreign Application Priority Data

Aug. 19, 2020 (GR) .............................. 20200100500

(51) Int. Cl.
*G16H 50/20* (2018.01)
*A61B 5/02* (2006.01)

(52) U.S. Cl.
CPC ............... *G16H 50/20* (2018.01); *A61B 5/02* (2013.01)

(58) Field of Classification Search
None
See application file for complete search history.

(56) References Cited

U.S. PATENT DOCUMENTS 7,396,331 B2 7/2008 Mack
8,165,893 B1 4/2012 Goldberg et al.
(Continued)

OTHER PUBLICATIONS

Borazio, et al., "Combining Wearable and Environmental Sensing into an Unobtrusive Tool for Long-Term Sleep Studies," IHI '12: Proceedings of the 2nd ACM Sighit International Health Informatics Symposium, Jan. 2012, pp. 71-80 https://doi.org/10.1145/21100363.2110375.

(Continued)

*Primary Examiner* — Jeffrey R Swearingen
(74) *Attorney, Agent, or Firm* — Arthur Shum

(57) ABSTRACT

In some embodiments, a method may include providing a system, where the system includes one or more physiological sensors and a micro-server that includes a communication interface, memory storing instructions, and a processor. The method may include instructing a subject to deploy the one or more sensors at a residence. The method may include receiving physiological data detected by the one or more sensors, storing data in the memory of the micro-server representative of the physiological data detected by the one or more sensors for later sharing. The method may include receiving an instruction to withhold an indicated set of the stored data from sharing and withholding the indicated set of the stored data from sharing. The withholding may include deleting the indicated set of the stored data from the memory of the micro-server and/or refraining from sending the indicated set of the stored data to an external device.

23 Claims, 10 Drawing Sheets

(56) References Cited

U.S. PATENT DOCUMENTS

| | | | | |
|---|---|---|---|---|
| 8,679,012 | B1 | 3/2014 | Hani | |
| 11,862,303 | B1 * | 1/2024 | Gershoni | G06N 3/006 |
| 11,984,220 | B2 * | 5/2024 | Yang | G16H 50/30 |
| 2002/0013906 | A1 | 1/2002 | Wallach et al. | |
| 2002/0049684 | A1 | 4/2002 | Nagamoto et al. | |
| 2015/0250385 | A1 | 9/2015 | Ahmed et al. | |
| 2015/0371516 | A1 | 12/2015 | Petersen et al. | |
| 2016/0213307 | A1 | 7/2016 | Mays et al. | |
| 2019/0223749 | A1 | 7/2019 | Toth et al. | |
| 2019/0392162 | A1 * | 12/2019 | Stern | G06F 21/6245 |
| 2020/0009349 | A1 | 1/2020 | Shouldice et al. | |
| 2022/0245812 | A1 * | 8/2022 | Newman-Toker | A61B 3/113 |
| 2022/0280040 | A1 * | 9/2022 | Javed | G16H 50/30 |
| 2022/0304603 | A1 * | 9/2022 | Freckleton | G16H 50/20 |
| 2022/0304622 | A1 * | 9/2022 | Freckleton | G16H 40/63 |
| 2024/0104907 | A1 * | 3/2024 | Mujica | G06V 10/803 |

OTHER PUBLICATIONS

Patent Cooperation Treaty International Search Report of the International Searching Authority pertaining to International Application No. PCT/US2021/046497; International Filing Date: Aug. 18, 2021; Date of Mailing: Dec. 2, 2021.

Patent Cooperation Treaty Written Opinion of the International Searching Authority pertaining to International Application No. PCT/US2021/046497; International Filing Date: Aug. 18, 2021; Date of Mailing: Dec. 2, 2021.

* cited by examiner

PHYSIOLOGICAL DATA MONITORING SYSTEM

FIELD OF THE DISCLOSURE

The present disclosure relates to a device and method for a physiological data monitoring system. More particularly, the present disclosure relates to a physiological data monitoring system for monitoring a subject during sleep and permitting the subject to withhold data recorded by the monitoring system from sharing and/or analysis.

BACKGROUND OF THE DISCLOSURE

Observational clinical studies, such as sleep studies, are typically conducted by asking a study participant to sleep at a location other than the study participant's home, such as a sleep laboratory. The sleep laboratory may include a room with sensors for recording data about the participant, such as an amount of movement at night, a heart rate, a temperature, or the like. The participant may be required to spend multiple nights at the sleep laboratory to obtain sufficient information for a sleep study, to diagnose an issue of the participant, or the like.

Requiring a study participant to visit a sleep laboratory or another location for a sleep study may be inconvenient for the participant, may risk spreading infection to other participants or researchers that use the sleep laboratory, may result in data that is not reflective of typical sleep patterns of the participant because the participant is not sleeping in their own home, may create privacy concerns associated with constant monitoring of the participant, and so on. To address these and other issues, a monitoring system may be set up at the participant's home. However, even with a home monitoring system, the participant may still lack the ability to control the data that is shared with researchers. Therefore, a need exists for methods and devices to address privacy concerns of study participants while still preserving data for researchers, healthcare providers, and/or data analysts.

SUMMARY

In some embodiments, a method for facilitating a subject to record physiological data regarding the subject and to allow the subject to withhold a subset of the recorded physiological data from sharing includes providing a system for the subject comprising: one or more physiological sensors, and a micro-server comprising at least one communication interface, memory storing instructions, and at least one processor; instructing the subject to deploy the one or more sensors at a residence of the subject to detect physiological data regarding the subject; receiving, by the micro-server via the at least one communication interface, the physiological data detected by the one or more sensors; storing, by the micro-server, data in the memory of the micro-server representative of the physiological data detected by the one or more sensors for later sharing; receiving, by the micro-server via the at least one communication interface, an instruction from the subject to withhold an indicated set of the stored data from sharing; and based on the received instruction, withholding the indicated set of the stored data from sharing, wherein said withholding comprises at least one of: (i) deleting the indicated set of the stored data from the memory of the micro-server, or (ii) refraining from sending the indicated set of the stored data to an external device.

In some embodiments, a method for facilitating a subject to record physiological data regarding the subject and to allow the subject to withhold a set of the recorded physiological data from sharing includes receiving, at a micro-server via a local wireless network, physiological data regarding the subject from one or more physiological sensors; storing, in memory at the micro-server, data representative of the physiological data; receiving, at the micro-server via the local wireless network, an indication from a mobile device regarding whether an indicated set of the stored data should be kept for sharing or withheld from sharing; and when the indication from the mobile device indicates that the indicated set of the stored data should be withheld from sharing: identifying the indicated set of the stored data to be withheld from sharing based on the indication, and withholding the indicated set of the stored data from sharing, said withholding comprising at least one of (i) deleting the indicated set of the stored data from memory at the micro-server, or (ii) refraining from sending the indicated set of the stored data to an external device.

In some embodiments, a method for facilitating a subject to record physiological data regarding the subject and to allow the subject to withhold a set of the recorded physiological data includes receiving, at a micro-server via a local wireless network, physiological data regarding the subject from one or more physiological sensors; storing, in memory at the micro-server, data representative of the physiological data; sending, from the micro-server to a remote server via a cellular network separate from the local wireless network, a notification that data representative of the physiological data has been stored in memory at the micro-server, wherein the notification causes the remote server to send, to a mobile device of the subject, via the cellular network, a request to confirm whether an indicated set of the stored data should be kept or withheld; receiving, from the remote server via the cellular network, an instruction to withhold the indicated set of the stored data when a response from the mobile device indicates that the indicated set of the stored data should be withheld; and in response to the instruction, withholding the indicated set of the stored data, said withholding comprising at least one of (i) deleting the indicated set of the stored data from the memory at the micro-server, or (ii) refraining from sending the indicated set of the stored data to the remote server.

In some embodiments, a micro-server includes one or more memories; and one or more processors, communicatively coupled to the one or more memories, configured to: receive, at the micro-server via a local wireless network, physiological data regarding the subject from one or more physiological sensors; store, in memory at the micro-server, data representative of the physiological data; receive, at the micro-server via the local wireless network, an indication from a mobile device regarding whether an indicated set of the stored data should be kept for sharing or withheld from sharing; and when the indication from the mobile device indicates that the indicated set of the stored data should be withheld from sharing: identify the indicated set of the stored data to be withheld from sharing based on the indication, and withhold the indicated set of the stored data from sharing, said withholding comprising at least one of (i) deleting the indicated set of the stored data from memory at the micro-server, or (ii) refraining from sending the indicated set of the stored data to an external device.

In some embodiments, a micro-server includes one or more memories; and one or more processors, communicatively coupled to the one or more memories, configured to: receive, at the micro-server via a local wireless network, physiological data regarding the subject from one or more physiological sensors; store, in memory at the micro-server, data representative of the physiological data; send, from the micro-server to a remote server via a cellular network separate from the local wireless network, a notification that data representative of the physiological data has been stored in memory at the micro-server, wherein the notification causes the remote server to send, to a mobile device of the subject, via the cellular network, a request to confirm whether an indicated set of the stored data should be kept or withheld; receive, from the remote server via the cellular network, an instruction to withhold the indicated set of the stored data when a response from the mobile device indicates that the indicated set of the stored data should be withheld; and in response to the instruction, withhold the indicated set of the stored data, said withholding comprising at least one of (i) deleting the indicated set of the stored data from the memory at the micro-server, or (ii) refraining from sending the indicated set of the stored data to the remote server.

In some embodiments, a non-transitory computer-readable medium storing a set of instructions includes one or more instructions that, when executed by one or more processors of a micro-server, cause the micro-server to: receive, at the micro-server via a local wireless network, physiological data regarding the subject from one or more physiological sensors; store, in memory at the micro-server, data representative of the physiological data; receive, at the micro-server via the local wireless network, an indication from a mobile device regarding whether an indicated set of the stored data should be kept for sharing or withheld from sharing; and when the indication from the mobile device indicates that the indicated set of the stored data should be withheld from sharing: identify the indicated set of the stored data to be withheld from sharing based on the indication, and withhold the indicated set of the stored data from sharing, said withholding comprising at least one of (i) deleting the indicated set of the stored data from memory at the micro-server, or (ii) refraining from sending the indicated set of the stored data to an external device.

In some embodiments, a non-transitory computer-readable medium storing a set of instructions includes one or more instructions that, when executed by one or more processors of a micro-server, cause the micro-server to: receive, at the micro-server via a local wireless network, physiological data regarding the subject from one or more physiological sensors; store, in memory at the micro-server, data representative of the physiological data; send, from the micro-server to a remote server via a cellular network separate from the local wireless network, a notification that data representative of the physiological data has been stored in memory at the micro-server, wherein the notification causes the remote server to send, to a mobile device of the subject, via the cellular network, a request to confirm whether an indicated set of the stored data should be kept or withheld; receive, from the remote server via the cellular network, an instruction to withhold the indicated set of the stored data when a response from the mobile device indicates that the indicated set of the stored data should be withheld; and in response to the instruction, withhold the indicated set of the stored data, said withholding comprising at least one of (i) deleting the indicated set of the stored data from the memory at the micro-server, or (ii) refraining from sending the indicated set of the stored data to the remote server.

In some embodiments, an apparatus includes means for receiving, at the apparatus via a local wireless network, physiological data regarding the subject from one or more physiological sensors; means for storing, in memory at the apparatus, data representative of the physiological data; means for receiving, at the apparatus via the local wireless network, an indication from a mobile device regarding whether an indicated set of the stored data should be kept for sharing or withheld from sharing; means for identifying the indicated set of the stored data to be withheld from sharing based on the indication, and means for withholding the indicated set of the stored data from sharing, said means for withholding comprising at least one of (i) means for deleting the indicated set of the stored data from memory at the apparatus, or (ii) means for refraining from sending the indicated set of the stored data to an external device.

In some embodiments, an apparatus includes means for receiving, at the apparatus via a local wireless network, physiological data regarding the subject from one or more physiological sensors; means for storing, in memory at the apparatus, data representative of the physiological data; means for sending, from the apparatus to a remote server via a cellular network separate from the local wireless network, a notification that data representative of the physiological data has been stored in memory at the apparatus, wherein the notification causes the remote server to send, to a mobile device of the subject, via the cellular network, a request to confirm whether an indicated set of the stored data should be kept or withheld; means for receiving, from the remote server via the cellular network, an instruction to withhold the indicated set of the stored data when a response from the mobile device indicates that the indicated set of the stored data should be withheld; and means for withholding the indicated set of the stored data based on the instruction, said means for withholding comprising at least one of (i) means for deleting the indicated set of the stored data from the memory at the apparatus, or (ii) means for refraining from sending the indicated set of the stored data to the remote server.

BRIEF DESCRIPTION OF THE DRAWINGS

The above-mentioned and other features and advantages of this disclosure, and the manner of attaining them, will become more apparent and will be better understood by reference to the following description of embodiments of the invention taken in conjunction with the accompanying drawings.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

The following detailed description of example embodiments refers to the accompanying drawings. The same reference numbers in different drawings may identify the same or similar elements.

Rather than requiring a participant in a physiological study (e.g., a sleep study) to visit a location other than the participant's home to perform the study, systems and methods described herein enable such a study to be performed in the participant's home. Some home sleep monitoring devices, such as mobile phones, bed sensors, or wearable devices, permit a user to monitor some embodiments of sleep behavior that are specific to the sensors associated with those home sleep monitoring devices. However, the data gathered by an individual device is often insufficient for a thorough sleep study, and the accuracy of sleep study results can be improved by gathering data from multiple independent devices that obtain different types of data and/or that obtain data using different types of sensors. Some embodiments described herein enable improved accuracy of study results and/or improved recommendations by enabling data to be gathered from multiple different sensors at a home of the user.

When physiological data is gathered using a home monitoring system, data security and data privacy issues may arise. To address data privacy and data security issues, some embodiments described herein may prevent data from being communicated and/or shared outside of a secure micro-server without consent from the user. Furthermore, some embodiments described herein permit the user to withhold (e.g., delete, refrain from transmitting, or the like) data that was recorded by the monitoring system. In a research study scenario, withholding all data may result in less accurate study result and/or worse recommendations. To address this issue, some embodiments described herein enable a user to withhold a specific portion of recorded data, such as data recorded from a particular sensor and/or at a particular time, and to approve sharing of remaining data with a researcher to enable accurate study results.

Figure 1A:
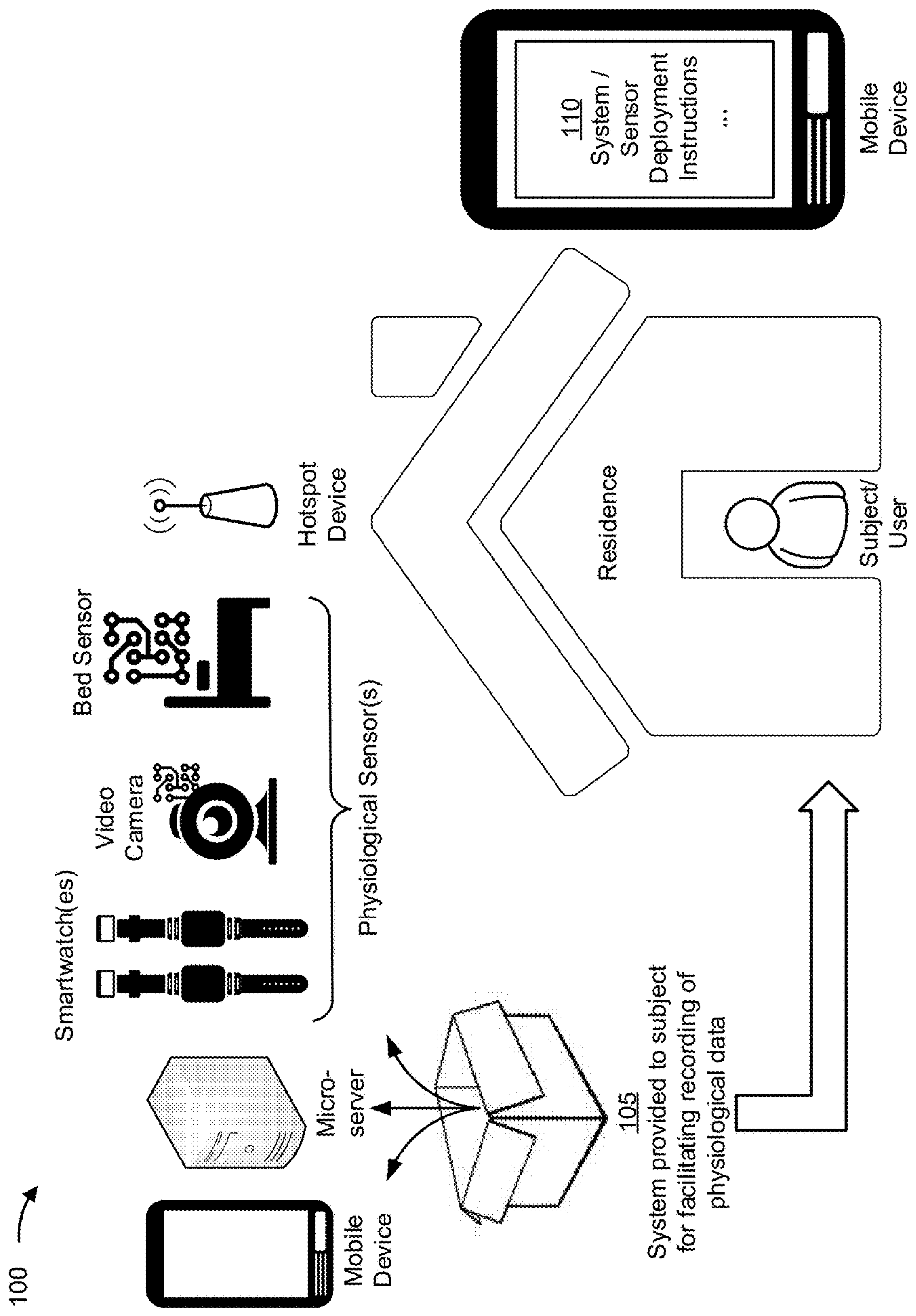
FIG. 1 is a diagram illustrating an example of setting up and using a physiological data monitoring system to monitor sleep behavior of a subject.

FIG. 1A is a diagram illustrating an example 100 of setting up and using a physiological data monitoring system to monitor sleep behavior of a subject. As shown in FIG. 1A, and by reference number 105, a system may be provided to a subject (e.g., a user, a study participant, or the like) to facilitate recording of physiological data of the subject. As shown, the system (e.g., a monitoring system) may include a mobile device, a micro-server, one or more physiological sensors (e.g., one or more smartwatches, a video camera, a bed sensor, or the like), and/or a hotspot device. These devices are described in more detail in connection with FIG. 4. The system is described as including these devices as an example, and the system may include more devices, fewer devices, and/or different devices than those illustrated in FIG. 1A. The system may be provided to the subject for use at the subject's home (e.g., residence). In some embodiments, the system may be delivered to the subject's home, may be provided to the subject at a location other than the subject's home and brought to the subject's home by the subject, or the like.

As shown by reference number 110, the subject may be provided with instructions for deploying (e.g., setting up) the system at the home of the subject. For example, the mobile device provided with the system may include or execute an application that provides instructions for the subject to deploy the system. The instructions may indicate, for example, how to set up one or more physiological sensors to monitor physiological data of the subject, how to set up the micro-server to enable collection of data from the one or more physiological sensors, how to set up the hotspot device to enable the micro-server to communicate with a remote server or another external device, or the like. In some embodiments, the mobile device may communicate with the micro-server, the one or more physiological sensors, and/or the hotspot device to obtain data as part of deploying the system. The mobile device may verify whether the system is properly set up based on the obtained data (e.g., by comparing data reported by a sensor with expected data or values associated with that sensor). If the mobile device determines that proper setup of a device included with the system could not be verified, then the mobile device may output additional instructions for the subject to properly deploy the device, may output contact information for technical support, or the like. Although FIG. 1A shows the instructions as being output via a mobile device provided with the system, in some embodiments, the instructions may be provided in another form, such as to a mobile device associated with or provided by the user and not provided with the system, in paper form, or the like.

Figure 1B:
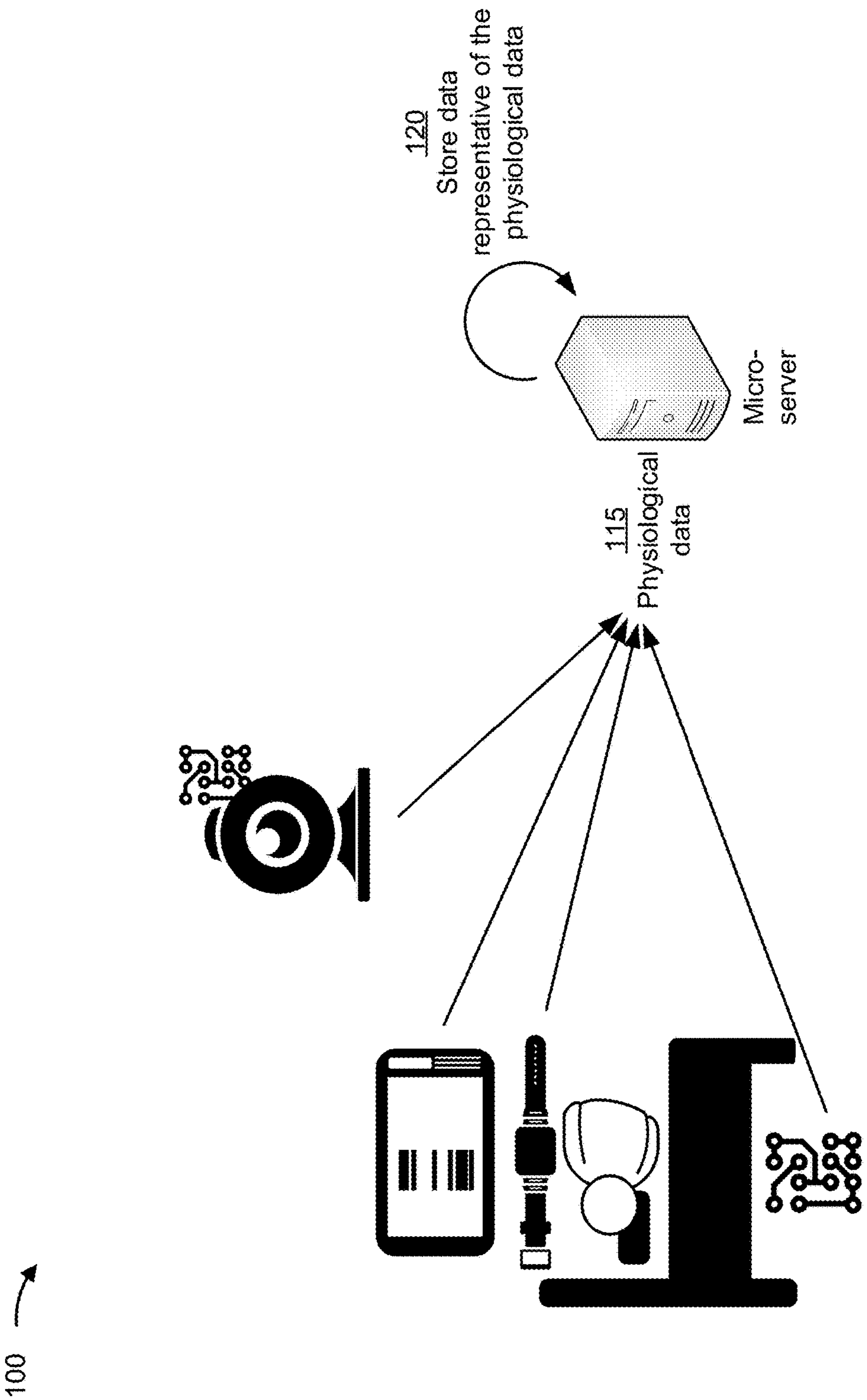

As shown in FIG. 1B, and by reference number 115, the micro-server may receive data (e.g., physiological data) from the one or more sensors, such as via a communication interface (e.g., a wireless communication interface). In some embodiments, gathering of data by the micro-server may be triggered. For example, when the subject is ready to sleep, the subject may interact with the mobile device to provide input that triggers the system to begin gathering data. The mobile device may transmit an instruction to the micro-server to initiate data gathering by the physiological sensors and/or to gather data from the physiological sensors (e.g., via wireless communication). Additionally, or alternatively, the mobile device and/or the micro-server may transmit an instruction to the physiological sensors to begin gathering data and transmitting that data to the micro-server. Once triggered, the system may continuously gather data until a pre-determined condition is satisfied, such as until user input is received (e.g., via the mobile device) instructing the system to stop gathering data, until a certain pre-programmed time period has passed, and/or until a certain pre-programmed time or date has been reached. For example, in embodiments directed to sleep studies, the subject may instruct or trigger the system to begin gathering data when the subject goes to sleep and allow the system to gather data continuously overnight. When the subject wakes up, the subject may instruct the system to stop gathering data.

The physiological data may include observable and/or measurable information about a manner in which a user's body functions. For example, the physiological data may include a video feed of the user's activities or movement, a heart rate of the user, a temperature associated with the user (e.g., a body temperature, a skin temperature, an environmental temperature, or the like), movement of the user (e.g., a speed of movement, a direction of movement, an amount of movement, or the like), a sleep measurement associated with the user (e.g., a quantity of hours slept, a sleep quality measurement based on movement of the user, actigraphy data indicative of the user's rest and activity cycles, or the like), a blood pressure of the user, a glucose level of the user (e.g., a blood glucose level), a pulse of the user, a quantity of steps taken by the user, a heat flux measurement associated with the user, a skin conductivity measurement associated with the user, a calorie measurement associated with the user (e.g., a quantity of calories burned), a moisture measurement associated with the user (e.g., a measurement of skin perspiration, a humidity measurement, or the like), a noise measurement associated with the user (e.g., due to movement of the user, scratching of the user's skin, vocalizations of the user, or the like), and/or a measurement of a chemical level associated with the user, among other examples.

As shown by reference number 120, the micro-server may store data representative of the physiological data in memory of the micro-server. The micro-server may store data locally in secure storage and may refrain from transmitting the data to another device until approval is received from the subject. In some embodiments, the micro-server may store the data in a structured format that enables differentiation among different types of physiological data, that enables differentiation among data received from different sensors, that enables differentiation among data received at different times or time periods, or the like. In this way, the micro-server may enable selection of specific data to be withheld (e.g., deleted, or flagged in a way that prevents transmission to an external device) and may retain the remaining data in memory (e.g., for use with a research study), thereby addressing data privacy issues while also retaining data useful for research, investigation, sharing, or analysis.

For example, upon receiving physiological data, the micro-server may identify a sensor from which the physiological data was received, may identify a type of the physiological data (e.g., heart rate data, movement data, temperature data, or the like), may determine a time at which the physiological data was received or recorded, may determine a time period during which the physiological data was recorded or measured, may determine a date on which the physiological data was recorded or measured, or the like. The micro-server may store the physiological data in association with metadata that indicates, for example, the sensor from which the physiological data was received, the physiological data type, the time, the time period, the date, or the like.

Figure 1C:
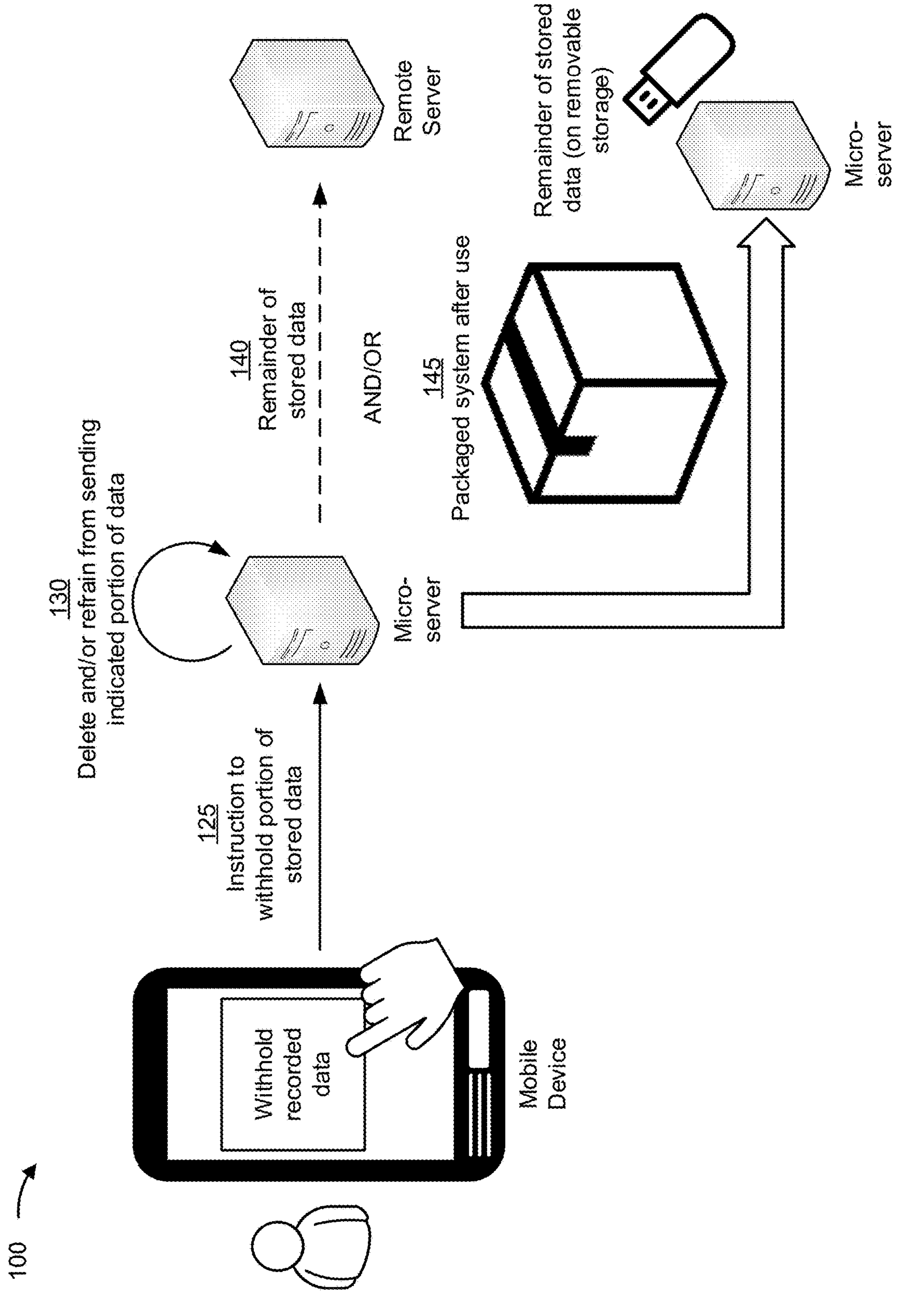

As shown in FIG. 1C, and by reference number 125, the micro-server may receive an instruction to withhold a portion of the stored data. For example, and as shown, a user may interact with a mobile device (e.g., the mobile device provided with the system or another mobile device associated with or provided by the user) to provide input indicating that data is to be withheld. Withholding the data may include, for example, deleting the data from memory of the micro-server, preventing the data from being transmitted by the micro-server to an external device (e.g., by excluding the data from a message transmitted by the micro-server), encrypting or password-protecting the data so as to prevent sharing with parties unable to decrypt the data, encrypting or password-protecting the data using an encryption key or password that is shared with or known to another party, storing the data in secure memory of the micro-server (e.g., in a different type of memory or a different memory location than data that is not being withheld), or the like. In some embodiments, the mobile device may prompt the user regarding whether to retain (e.g., keep) or withhold recorded information and may receive the input from the user based on the prompt. For example, the mobile device may prompt the user at a particular time, may prompt the user upon detecting that the user is awake, may prompt the user upon receiving user input instructing the system to stop gathering and/or recording data, or may prompt the user based on some other condition (e.g., detecting that the user is awake and that the time is 7:00 a.m. or later). In some embodiments, the user may be prompted regarding whether to withhold all recently recorded data and/or to confirm whether recently recorded data should be kept (e.g., for sharing, for analysis, for transmission to an external device, or the like), such as whether to withhold all data recorded the prior night. Additionally, or alternatively, the user may be prompted to select data to be withheld, as described in more detail below in connection with FIG. 2. In some embodiments, the mobile device may communicate directly with the micro-server to provide the instruction, such as via a wireless signal transmitted via a short-range wireless communication interface (e.g., via a Wi-Fi interface, via a near-field communication (NFC) interface, or via a wireless local area network), or the like. Alternatively, the mobile device may communicate with the micro-server via a remote server or another external device (e.g., via a long-range wireless communication interface, such as a cellular interface, over a cellular network, or the like), as described in more detail below in connection with FIG. 3.

Although FIG. 1C shows a user interacting with a mobile device to provide an instruction to the micro-server to withhold a portion of the stored data, another mechanism may be used to enable the user to cause withholding of data by the micro-server. For example, the micro-server may include one or more input components (e.g., one or more buttons, touch screens, physical actuators, or the like) with which a user can interact to instruct the micro-server to withhold a portion of the stored data. In some embodiments, the micro-server may include one or more output components (e.g., one or more screens, touch screens, speakers, light-emitting diodes, and/or the like) to prompt a user regarding withholding of data, in a similar manner as described in connection with prompting the user regarding withholding of data using a mobile device. The one or more input components and/or the one or more output components may be located on a housing of the micro-server. Furthermore, rather than the user indicating a portion of data to be withheld, the user may indicate a portion of data to be retained (e.g., data to be kept, data that is not to be deleted from memory, data that is to be transmitted to an external device, data that is not encrypted and/or password-protected, data that is encrypted or password-protected using an encryption key or a password shared with or known to another party, and/or the like). In some embodiments, a remaining portion of data that is not retained may be withheld. Thus, the micro-server may identify the data to be withheld based on an indicated of data to be retained (e.g., where the data to be withheld does not include the data to be retained).

As shown by reference number 130, the micro-server may withhold the indicated portion of data from memory. In FIG. 1C, the withholding is shown as deleting the indicated portion of data and refraining from transmitting the indicated portion of data. As described above, the micro-server may store physiological data in association with metadata and may use the metadata to identify the physiological data to be deleted (or otherwise withheld). For example, if the micro-server receives an instruction to withhold video data recorded between 10:00 p.m. and 11:00 p.m. the previous night (e.g., on a particular date), then the micro-server may identify physiological data stored in association with metadata indicating a video data type and a time period that includes a period between 10:00 p.m. and 11:00 p.m. on the indicated date. The micro-server may delete the identified physiological data (e.g., the video data) while retaining other physiological data recorded in connection with the subject. For example, the micro-server may retain heart rate data recorded between 10:00 p.m. and 11:00 p.m. on the indicated date, may retain temperature data recorded between 10:00 p.m. and 11:00 p.m. on the indicated date, and so on.

In some embodiments, the micro-server may delete or withhold an entire file that includes the indicated data. Continuing with the above example, the micro-server may delete or withhold an entire video file containing video data recorded between 10:00 p.m. and 11:00 p.m. on the indicated date even if the file also includes video data recorded at other times that are not between 10:00 p.m. and 11:00 p.m. on the indicated date. This may reduce complexity and conserve processing and memory resources of the micro-server. Alternatively, the micro-server may only delete or withhold video data recorded between 10:00 p.m. and 11:00 p.m. on the indicated date and may retain other video data stored in the file. For example, the micro-server may divide a file into multiple files associated with different time periods to enable fine-grained deletion or withholding of data. In some embodiments, the micro-server may periodically receive data from a physiological sensor, and may store data received at different times in different files to enable fine-grained deletion or withholding of data associated with a particular time period, rather than deletion or withholding of, for example, data associated with an entire night. In this way, more data may be retained for sharing and/or analysis.

As shown by reference number 140, the micro-server may transmit a remaining portion of stored data (e.g., an undeleted portion, a retained portion, or the like) to a remote server (e.g., an external device at a remote location different from the location of the micro-server). In some embodiments, the micro-server may transmit the remaining portion of stored data only after receiving input from a user approving such transmission. For example, the micro-server and/or the remote server may communicate with the mobile device to cause the mobile device to output a prompt for the user to approve transmission of retained data stored by the micro-server. This prompt may be triggered periodically (e.g., at a particular time of day, on a particular day of the week, or the like), may be triggered based on a condition being satisfied (e.g., less than a threshold amount of percentage of available memory of the micro-server), may be initiated by the user or a research interacting with the remote server (e.g., via a web site), or the like. The user may interact with the mobile device to approve or deny transmission of data, and the micro-server may act accordingly by transmitting the data or refraining from transmitting the data based on the user input.

In some embodiments, rather than refraining from transmitting the indicated portion of data, the micro-server may encrypt and/or password-protect the data to be withheld and may refrain from encrypting and/or password-protecting the data to be retained. In this case, the micro-server may transmit both the data to be withheld and the data to be retained to an external device, and a party that obtains this data (e.g., via the external device) may be able to access the data to be retained and may be unable to access the data to be withheld (e.g., because the party does not have an encryption key and/or password required to obtain the data to be withheld). Alternatively, the micro-server may encrypt and/or password-protect the data to be withheld using a first encryption key or a first password that is not shared with or known by the party, and may encrypt and/or password-protect the data to be retained using a second encryption key or a second password that is shared with or known by the party. In this case, the micro-server may transmit both the data to be withheld and the data to be retained to an external device, and a party that obtains this data (e.g., via the external device) may be able to access the data to be retained (e.g., using the second encryption key or the second password) and may be unable to access the data to be withheld (e.g., because the party does not have the first encryption key and/or the first password).

Additionally, or alternatively, as shown by reference number 145, the user may provide the system, including the micro-server, to a researcher (or another party or entity) to enable the researcher analyze the data. For example, the user may package the system after physiological data has been recorded and may mail or drop off the system to a location associated with the researcher, or the researcher may otherwise retrieve the micro-server from the user. In some embodiments, instead of mailing or dropping off the entire system, the user may mail or drop off only the removable storage (e.g., a USB drive or hard drive) provided with the system to the researcher. As shown, the researcher may obtain the stored data, such as by retrieving or downloading the stored data from removable storage that includes the memory on which the data was stored by the micro-server. By enabling a user to withhold a portion of data, sensitive user data can be withheld while also retaining data useful for research, investigation, sharing, or analysis.

As indicated above, FIGS. 1A-1C are provided as an example. Other examples may differ from what is described with regard to FIGS. 1A-1C. The number and arrangement of devices shown in FIGS. 1A-1C are provided as an example. In practice, there may be additional devices, fewer devices, different devices, or differently arranged devices than those shown in FIGS. 1A-1C. Furthermore, two or more devices shown in FIGS. 1A-1C may be implemented within a single device, or a single device shown in FIGS. 1A-1C may be implemented as multiple, distributed devices. Additionally, or alternatively, a set of devices (e.g., one or more devices) shown in FIGS. 1A-1C may perform one or more functions described as being performed by another set of devices shown in FIGS. 1A-1C.

Figure 2:
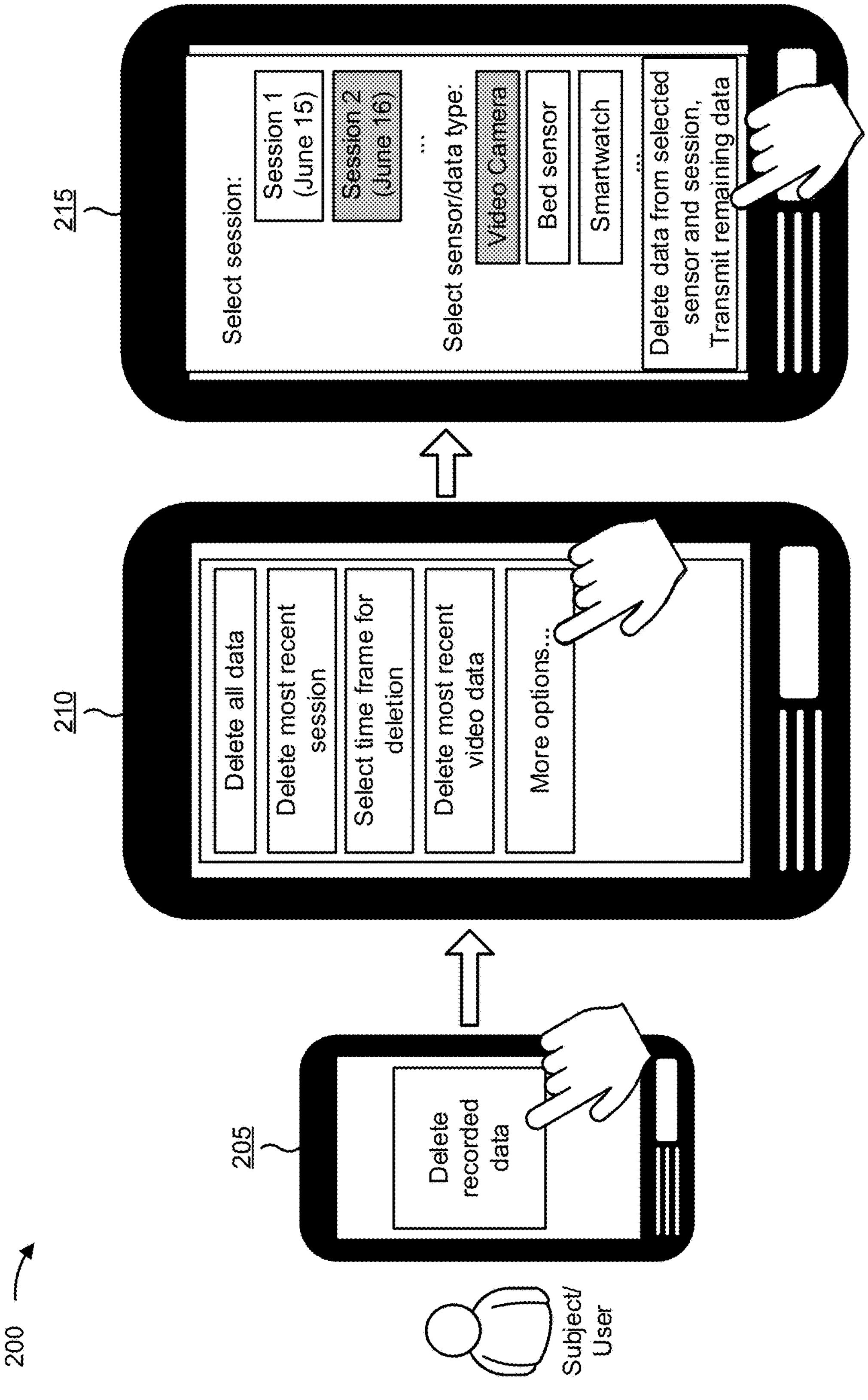
FIG. 2 is a diagram illustrating an example of enabling a subject to control data that is shared with a researcher or another party.

FIG. 2 is a diagram illustrating an example 200 of enabling a subject to control data that is shared with a researcher or another party. As shown by reference number 205, a mobile device (e.g., provided with a monitoring system and/or associated with a user) may provide a user interface or another input mechanism that enables a user to interact with the mobile device to indicate data to be deleted from memory of a micro-server. Although FIG. 2 is described in connection with deleting data, the data may be withheld in a different manner other than or in addition to deletion, as described above in connection with FIG. 1C. In some embodiments, the user may navigate to the user interface by interacting with the mobile device. Additionally, or alternatively, the user interface may be provided for display based on a trigger, as described above in connection with FIG. 1C.

As shown by reference number 210, in some embodiments, the mobile device may provide a user interface that enables the user to delete all data stored by the micro-server and/or to select a portion of data to be deleted from the micro-server. For example, the user may provide input to delete all data recorded in the most recent recording session. Additionally, or alternatively, the user may select a time period (e.g., a time frame) and instruct the micro-server to delete data (or a portion of data) recorded during that time period. Additionally, or alternatively, the user may provide input to select a type of physiological data to be deleted and instruct the micro-server to delete data of the indicated type.

Additionally, or alternatively, the user may provide input to select a type of sensor or a particular sensor and instruct the micro-server to delete data received from that type of sensor or that particular sensor.

As an example, and as shown by reference number 215, the user may select a date (or a span of dates), which may be associated with a particular recording session (e.g., a night-time recording), and may select a type of physiological data to be deleted (e.g., shown as data received from a video camera). Based on user interaction with the mobile device to select these parameters for data deletion, the mobile device may transmit the parameters to the micro-server (e.g., directly or indirectly, as described elsewhere herein). Based on receiving the parameters, the micro-server may delete the indicated data (e.g., data stored in association with metadata that matches or satisfies a condition indicated by the parameters), as described above in connection with FIG. 1C.

As indicated above, FIG. 2 is provided as an example. Other examples may differ from what is described with regard to FIG. 2. For example, different user interfaces or input components may be used to select data for deletion.

Figure 3:
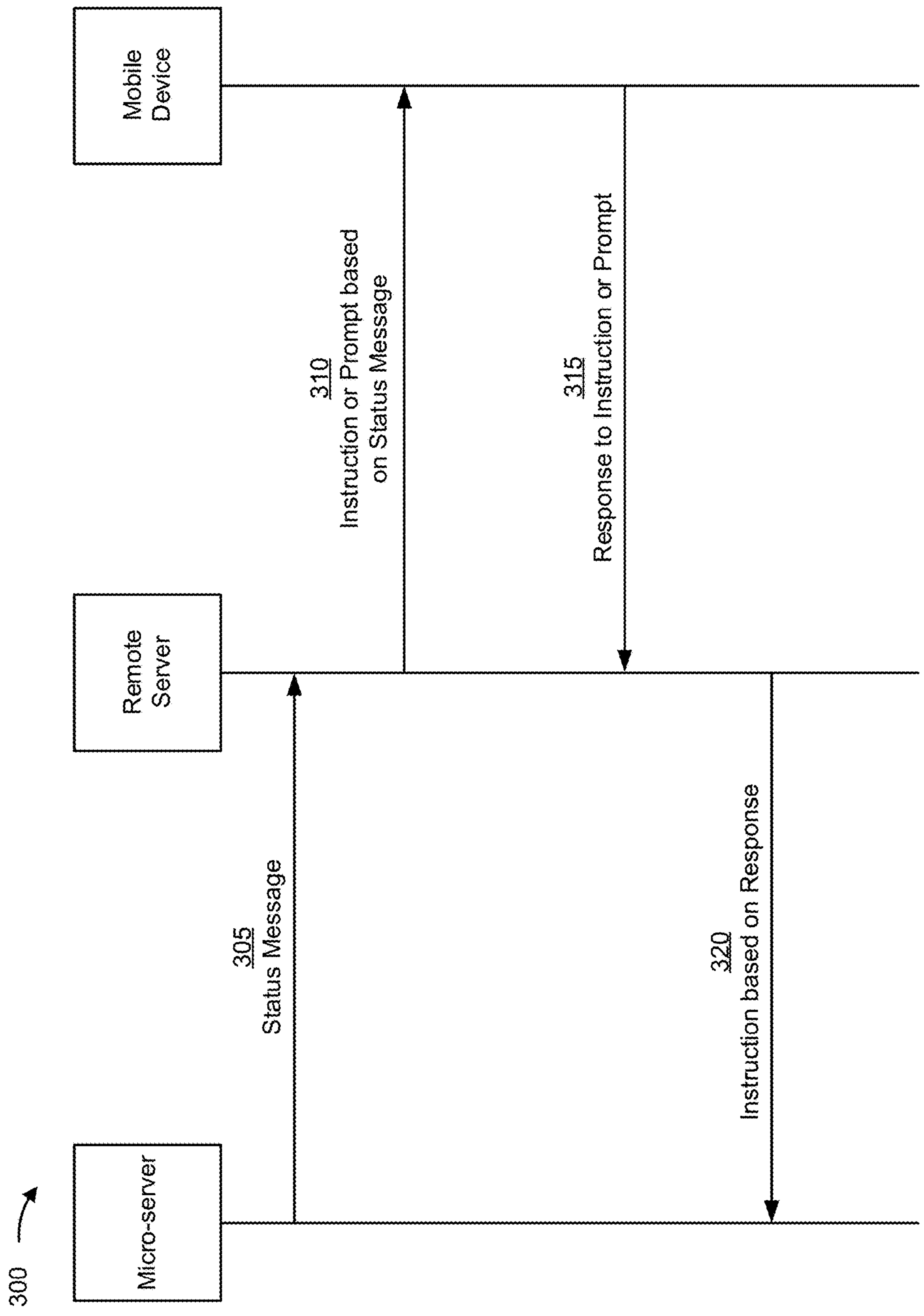
FIG. 3 is a diagram illustrating an example of communications among a micro-server that collects physiological data of a subject, a remote server that monitors a status of the micro-server, and a mobile device associated with the subject.

FIG. 3 is a diagram illustrating an example 300 of communications among a micro-server that collects physiological data of a subject, a remote server (e.g., an external device) that monitors a status of the micro-server, and a mobile device associated with the subject. The micro-server, the remote server, and the mobile device are described in more detail in connection with FIG. 4.

As shown by reference number 305, the micro-server may transmit a status message to the remote server (e.g., via a long-range wireless communication interface, via a cellular network, or the like). The micro-server may transmit a status message periodically, may transmit a status message based on a request received from the remote server, may transmit a status message based on a condition being satisfied, or the like. The status message may indicate a state of the micro-server. For example, the status message may include a message that indicates a power status of one or more of the physiological sensors (e.g., a battery charge of a sensor, a remaining battery level of a sensor, whether the sensor is powered on, whether the sensor is connected to alternating current (AC) power, or the like). Additionally, or alternatively, the status message may indicate a connection status between one or more physiological sensors and the micro-server (e.g., whether the micro-server is receiving data from a sensor, whether the micro-server can detect the sensor via a network connection, or the like). Additionally, or alternatively, the status message may include a notification that the micro-server has stored physiological data available for transmission to the remote server. Additionally, or alternatively, the status message may indicate a memory status of the micro-server (e.g., an amount of recorded data and/or a remaining unfilled memory capacity, a number of recording sessions completed, an aggregate number of hours or minutes recorded, or the like).

As shown by reference number 310, the remote server may transmit an instruction and/or a prompt to the mobile device based on the status message (e.g., via a long-range wireless communication interface, via a cellular network, or the like). In some embodiments, the remote server may transmit, to the mobile device, instructions to troubleshoot an issue indicated in the status message. For example, if the status message indicates that a sensor has a low battery level, then the remote server may transmit an instruction for a user of the mobile device to plug in the sensor, to check a charging status of the sensor, or the like. As another example, if the status message indicates that the sensor and the micro-server do not have a network connection, then the remote server may transmit an instruction for a user of the mobile device to check a network setting associated with the micro-server and/or the sensor.

As another example, if the status message indicates that the micro-server has stored physiological data available for transmission to the remote server, then the remote server may transmit information that causes the mobile device to output a prompt for the user regarding whether to approve transmission of the data to the remote server, to confirm whether data or a portion of data stored by the micro-server should be deleted or withheld, or the like. The prompt may be the same as or similar to what is described above in connection with FIG. 2.

As shown by reference number 315, the mobile device may transmit a response to the remote server based on the instruction or the prompt (e.g., via a long-range wireless communication interface, via a cellular network, or the like). For example, the mobile device may provide a user interface for display based on the instruction or the prompt and may receive user input via the user interface. The user input may indicate, for example, that troubleshooting of an issue is complete, that an issue has been resolved, that transmission of physiological data to the remote server is approved or denied, that a portion of stored data should be deleted or withheld, or the like.

As shown by reference number 320, the remote server may transmit an instruction to the micro-server based on the response (e.g., via a long-range wireless communication interface, via a cellular network, or the like). As an example, for an issue that needs troubleshooting, the remote server may instruct the micro-server to verify a power status of a sensor, to check a connection with a sensor, or the like (e.g., if the response from the mobile device indicates that the issue has been resolved). As another example, if the micro-server has data available for transmission to the remote server and the response from the mobile device indicates approval to transmit the data, then the remote server may instruct the micro-server to transmit the data to the remote server. As another example, if the response indicates data to be withheld or deleted from memory of the micro-server, then the remote server may instruct the micro-server to withhold the indicated data, to delete the indicated data from memory, and/or to transmit a remaining portion of data (e.g., via a long-range wireless communication interface, via a cellular network, or the like), in a similar manner as described elsewhere herein.

The micro-server may transmit stored data to the remote server only when the response and/or the instruction indicates that the stored data should be retained. Otherwise, if the response and/or the instruction indicates that stored data should be withheld, should be deleted, and/or should not be kept, then the micro-server may withhold the stored data or may delete the stored data from memory. In some embodiments, the response and/or the instructions may indicate a first portion of data to be withheld or deleted and a second portion of data to be kept. In this case, the micro-server may withhold or delete the first portion of data, and the micro-server may transmit the second portion of data to the remote server (or may maintain the second portion of data in memory for later retrieval). By enabling a user to withhold a portion of data, sensitive user data can be withheld while also retaining data useful for research, investigation, sharing, or analysis.

As indicated above, FIG. 3 is provided as an example. Other examples may differ from what is described with regard to FIG. 3.

Figure 4:
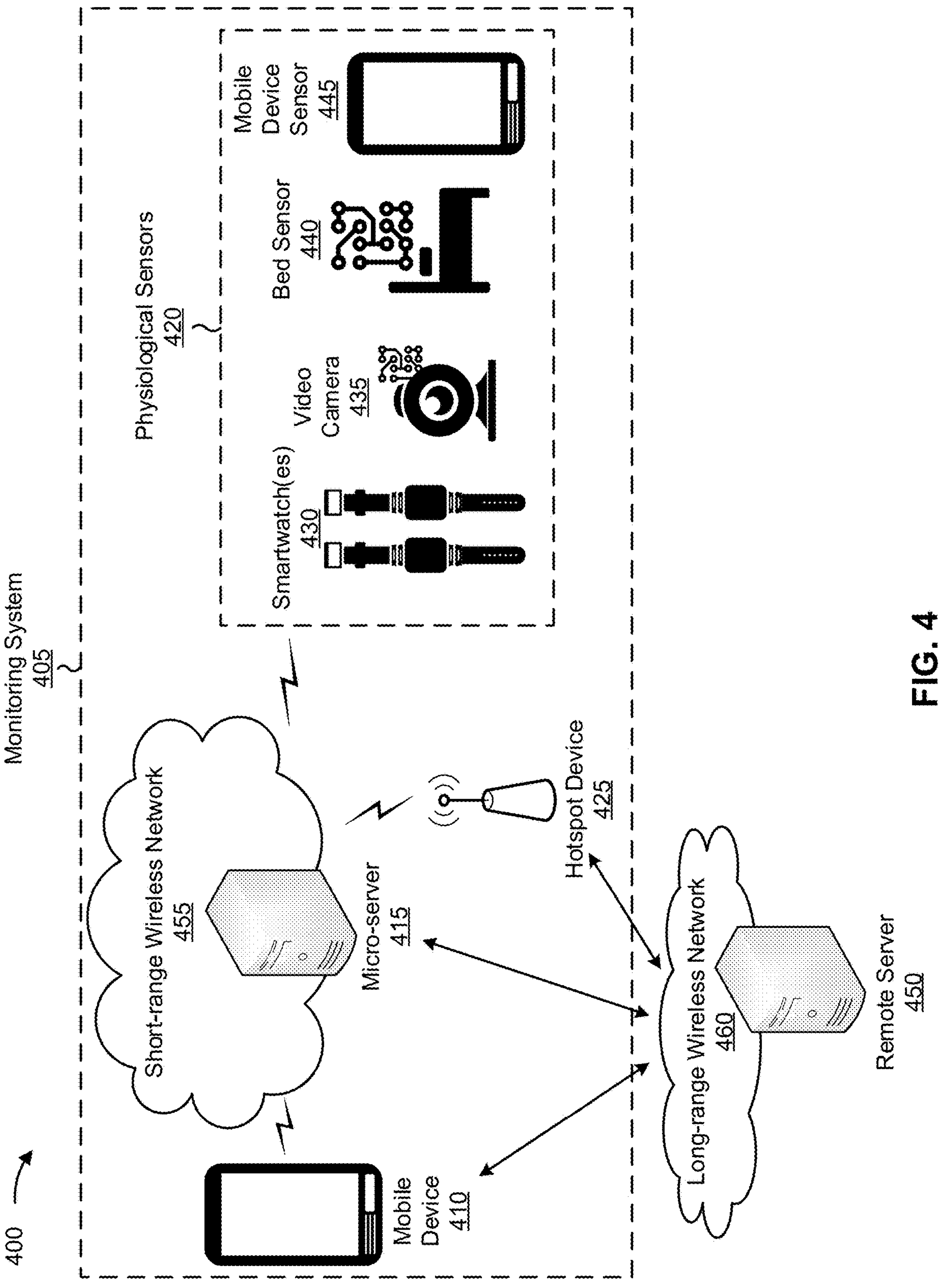
FIG. 4 is a diagram illustrating an example environment in which systems and/or methods described herein may be implemented.

FIG. 4 is a diagram of an example environment 400 in which systems and/or methods described herein may be implemented. As shown in FIG. 4, environment 400 may include a monitoring system 405. The monitoring system 405 may include, for example, mobile device 410, a micro-server 415, one or more physiological sensors 420, and/or a hotspot device 425. As shown, the one or more physiological sensor 420 may include one or more smartwatches 430, a video camera 435, a bed sensor 440, and/or a mobile device sensor 445. As further shown, environment 400 may include a remote server 450, a short-range wireless network 455, and a long-range wireless network 460. Devices of environment 400 may interconnect via wired connections, wireless connections, or a combination of wired and wireless connections.

The monitoring system 405 may correspond to the system provided to the subject or user, as described above in connection with FIGS. 1A-1C. The monitoring system 405 may be provided to the subject and deployed by the subject at a residence of the subject to detect physiological data regarding the subject. The monitoring system 405 may measure, sense, and/or obtain the physiological data using the one or more physiological sensors 420, which may provide the physiological data to the micro-server 415.

The mobile device 410 includes one or more devices capable of receiving, generating, storing, processing, outputting, and/or transmitting information associated with deployment and/or use of the monitoring system 405, as described elsewhere herein. The mobile device 410 may include a communication device and/or a computing device. For example, the mobile device 410 may include a mobile smartphone, a cell phone, a wireless communication device, a user equipment (UE), a laptop computer, a tablet computer, a handheld computer, a wearable communication device (e.g., a smart wristwatch or a pair of smart eyeglasses, among other examples), or a similar type of device. The mobile device 410 may communicate with one or more other devices of environment 400, as described elsewhere herein. In some embodiments, the mobile device 410 may be provided with the monitoring system 405 and may include one or more physiological sensors 420. For example, in some embodiments, the mobile device 410 may be the same device as, and perform the functions of, mobile device sensor 445 (described in further detail below). Alternatively, the mobile device 410 may be a personal mobile device of the user and may not be provided with the monitoring system 405.

The micro-server 415 includes one or more devices capable of receiving, storing, deleting, withholding, processing, and/or transmitting physiological data, as described elsewhere herein. The micro-server 415 may include a communication device and/or a computing device. For example, the micro-server 415 may include a server, a smartphone, a personal computer (PC), a laptop, a tablet, a system on a chip (SoC), or a similar type of device. As described in more detail below in connection with FIG. 5, the micro-server 415 may include at least one processor, memory storing instructions, at least one communication interface and/or communication component (e.g., at least one wireless communication interface and/or wireless communication component), or the like. In some embodiments, the micro-server 415 includes a short-range wireless communication interface to communicate via the short-range wireless network 455 and a long-range wireless communication interface to communicate via the long-range wireless network 460. For example, the micro-server 415 may communicate with the one or more physiological sensors 420, the mobile device 410, and/or the hotspot device 425 via the short-range wireless network 455. Additionally, or alternatively, the micro-server 415 may communicate with the remote server 450 via the long-range wireless network 460. In some embodiments, the micro-server 415 includes one or more input components (e.g., physical actuators) on a housing of the micro-server 415. In some embodiments, the micro-server 415 may be integrated with one or more other components shown in FIG. 4, such as mobile device 410, hotspot device 425, and/or one or more of the physiological sensors 420.

A physiological sensor 420 includes one or more devices capable of receiving, measuring, sensing, generating, storing, processing, outputting, and/or transmitting physiological data associated with a subject or user. Physiological data may include observable and/or measurable information about a manner in which the person's body functions, sometimes referred to as a biological indicator. For example, the physiological data may include a video feed of the user's movements or activities, a heart rate of a user, a temperature associated with the user (e.g., a body temperature, a skin temperature, an environmental temperature, or the like), movement of the user (e.g., a speed of movement, a direction of movement, an amount of movement, or the like), a sleep measurement associated with the user (e.g., a quantity of hours slept, a sleep quality measurement based on movement of the user, actigraphy data indicative of the user's rest and activity cycles, or the like), a blood pressure of the user, a glucose level of the user (e.g., a blood glucose level), a pulse of the user, a quantity of steps taken by the user, a heat flux measurement associated with the user, a skin conductivity measurement associated with the user, a calorie measurement associated with the user (e.g., a quantity of calories burned), a moisture measurement associated with the user (e.g., a measurement of skin perspiration, a humidity measurement, or the like), a noise measurement associated with the user (e.g., due to movement of the user, scratching of the user's skin, vocalizations of the user, or the like), and/or a measurement of a chemical level associated with the user, among other examples.

Physiological data may be measured and/or captured by a physiological sensor 420. The physiological sensor 420 may include, for example, a video camera, a heart rate monitor, a temperature sensor (e.g., a skin temperature sensor, an air temperature sensor, or the like), a sleep monitor, a blood pressure sensor, a ballistocardiography sensor (e.g., to sense ejection of blood into blood vessels due to a heart beat), an actigraphy sensor (such as a wrist-mounted actigraphy sensor or a body-mounted actigraphy sensor to monitor the user's rest/activity cycles), a bed vibration sensor, a breathing sensor (e.g., to detect a breathing rate, a breath volume, or the like), a glucose monitor, a pulse monitor, an accelerometer, a pedometer, a gyroscope, a heat flux sensor, a skin conductivity sensor, a calorie monitor, a motion sensor, a moisture sensor (e.g., a perspiration sensor), a chemical sensor or chemical compound sensor (e.g., to measure oxygen, carbon dioxide, lactate, testosterone, cortisol, glucose, glucagon, glycogen, insulin, starch, free fatty acid, triglycerides, monoglycerides, glycerol, pyruvate, lipids, other carbohydrates, ketone bodies, choline, or the like), and/or an audio recording device (e.g., a microphone, an ambient audio recording device, a wearable audio recording device, or the like, which may detect noises from scratching by the user, from movement of the user, from the user's snoring, from a user's stomach, a burp, passing gas, noises from a bathroom, or the like), among other examples. In some embodiments, a physiological sensor 420 may measure or sense a parameter other than a biological indicator, such as an environmental parameter.

In some embodiments, one or more of the above physiological sensors 420 may be integrated into a device, such as one or more smartwatches 430 (e.g., two smartwatches, one for the user's right hand and one for the user's left hand), a video camera 435 (e.g., which may include an actuator and/or input component to permit a camera to be blocked or unblocked), a bed sensor 440, a mobile device sensor 445, or the like. For example, the smartwatch 430 may include an actigraphy sensor (e.g., a wrist-mounted actigraphy sensor), a heart rate monitor, a movement sensor, a sleep monitor, a temperature sensor, a skin conductivity sensor, a pulse monitor, an accelerometer, a gyroscope, a moisture sensor, and/or a microphone. As another example, the video camera 435 may include a camera (e.g., to record movement of the user) and/or a microphone. As another example, the bed sensor 440 may include a sleep quality monitor, a ballistocardiography sensor, a breathing sensor, a bed vibration sensor, and/or a movement sensor. As another example, the mobile device sensor 445 may include a movement sensor, a sleep monitor, a temperature sensor, an accelerometer, a gyroscope, and/or a microphone. In some embodiments, additional devices than those shown in FIG. 4, fewer devices than those shown in FIG. 4, different devices than those shown in FIG. 4, or a different combination of devices than those shown in FIG. 4 may be included in the monitoring system 405 and may house the physiological sensors 420 described herein. In some embodiments, the mobile device sensor 445 may be integrated into the mobile device 410.

The hotspot device 425 includes one or more devices capable of communicating with one or more devices of the monitoring system 405 (e.g., micro-server 415) via the short-range wireless network 455 and capable of communicating with the remote server 450 via the long-range wireless network 460. For example, the hotspot device 425 may include a short-range wireless communication interface to communicate via the short-range wireless network 455 and a long-range wireless communication interface to communicate via the long-range wireless network 460. In some embodiments, the hotspot device 425 is integrated into the micro-server 415. In some embodiments, the hotspot device 425 is separate from the micro-server 415.

The remote server 450 includes one or more devices capable of communicating with the mobile device 410, the micro-server 415, and/or the hotspot device 425 to obtain physiological data, check a status of the micro-server 415, assist with resolving issues of the micro-server 415, assist with deletion or withholding of data from the micro-server 415, or the like, as described elsewhere herein. The remote server 450 may include a communication device and/or a computing device. For example, the remote server 450 may include a server, an application server, a client server, a web server, a database server, a host server, a proxy server, a virtual server (e.g., executing on computing hardware), a server in a cloud computing system, a device that includes computing hardware used in a cloud computing environment, or a similar type of device. The remote server 450 may communicate with the mobile device 410, the micro-server 415, and/or the hotspot device 425 via one or more networks, which may include the long-range wireless network 460. The remote server 450 is an example of an external device with which the micro-server 415 may communicate.

The short-range wireless network 455 includes one or more wireless networks designed for short-range communication, such as a wireless local area network (WLAN) (e.g., a Wi-Fi network), a wireless personal area network (WPAN) (e.g., a Bluetooth network), a near-field communication (NFC) network, or the like. The short-range wireless network 455 enables communication between, for example, the micro-server 415 and the physiological sensors 420, the micro-server 415 and the hotspot device 425, and/or the micro-server 415 and the mobile device 410. In some embodiments, devices of environment 400 may communicate via the short-range wireless network 455 using a representational state transfer (REST) protocol.

The long-range wireless network 460 includes one or more wireless networks designed for long-range communication, such as a wireless wide area network (WWAN), a cellular network (e.g., a fifth generation (5G) network, a fourth generation (4G) network, a long-term evolution (LTE) network, a third generation (3G) network, a code division multiple access (CDMA) network, or the like). In some embodiments, the long-range wireless network 460 may include and/or may communicate with a wired network, such as via a wired backhaul connection between a radio access network access point and a core network, via a wired connection between one or more devices of the core network, or the like. The long-range wireless network 460 enables communication between, for example, the micro-server 415 and the remote server 450, the hotspot device 425 and the remote server 450, and/or the mobile device 410 and the remote server 450.

The number and arrangement of devices and networks shown in FIG. 4 are provided as an example. In practice, there may be additional devices and/or networks, fewer devices and/or networks, different devices and/or networks, or differently arranged devices and/or networks than those shown in FIG. 4. Furthermore, two or more devices shown in FIG. 4 may be implemented within a single device, or a single device shown in FIG. 4 may be implemented as multiple, distributed devices. Additionally, or alternatively, a set of devices (e.g., one or more devices) of environment 400 may perform one or more functions described as being performed by another set of devices of environment 400.

Figure 5:
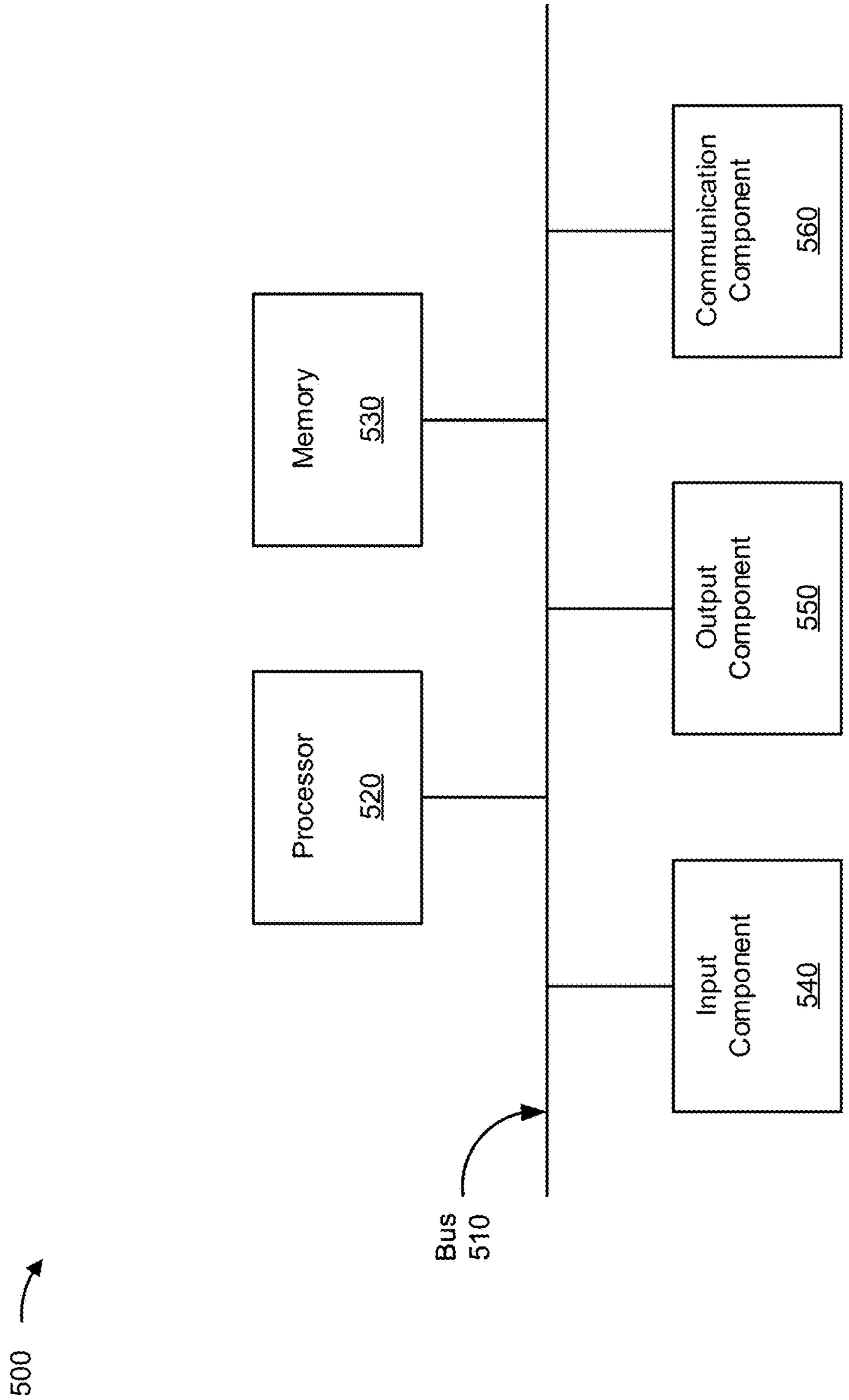
FIG. 5 is a diagram illustrating example components of one or more devices of FIG. 4.

FIG. 5 is a diagram of example components of a device 500, which may correspond to the mobile device 410, the micro-server 415, one or more physiological sensors 420 (e.g., the smartwatch 430, the video camera 435, the bed sensor 440, and/or the mobile device sensor 445), the hotspot device 425, and/or the remote server 450. In some embodiments, the mobile device 410, the micro-server 415, one or more physiological sensors 420, the hotspot device 425, and/or the remote server 450 may include one or more devices 500 and/or one or more components of device 500. As shown in FIG. 5, device 500 may include a bus 510, a processor 520, a memory 530, an input component 540, an output component 550, and a communication component 560.

Bus 510 includes a component that enables wired and/or wireless communication among the components of device 500. Processor 520 includes a central processing unit, a graphics processing unit, a microprocessor, a controller, a microcontroller, a digital signal processor (DSP), a field-programmable gate array (FPGA), an application-specific integrated circuit (ASIC), hardwired logic, and/or another type of processing component. Processor 520 is implemented in hardware, firmware, or a combination of hardware and software. In some embodiments, processor 520 includes one or more processors (e.g., at least one processor) capable of being programmed to perform a function. Memory 530 includes volatile and/or non-volatile memory. For example, memory 530 may include a random access memory (RAM), a read only memory (ROM), an electrically erasable programmable ROM (EEPROM), a hard disk drive, and/or another type of memory (e.g., a flash memory, a magnetic memory, and/or an optical memory). Memory 530 may include internal memory (e.g., RAM, ROM, a hard disk drive) and/or removable memory (e.g., removable via a universal serial bus connection). Memory 530 may be a non-transitory computer-readable medium. Memory 530 stores information, instructions, and/or software (e.g., one or more software applications) related to the operation of device 500. The term "logic" or "application" as used herein may include software and/or firmware executing on one or more processors. Therefore, in accordance with the embodiments, various logic may be implemented in any appropriate fashion and would remain in accordance with the embodiments herein disclosed.

Input component 540 enables device 500 to receive input, such as user input and/or sensed inputs. For example, input component 540 may include a touch screen, a keyboard, a keypad, a mouse, a button, a microphone, a switch, a sensor, a global positioning system component, an accelerometer, a gyroscope, an actuator, and/or the like. Output component 550 enables device 500 to provide output, such as via a display, a speaker, and/or one or more light-emitting diodes. Communication component 560 enables device 500 to communicate with other devices, such as via a wired connection and/or a wireless connection. For example, communication component 560 may include a receiver, a transmitter, a transceiver, a modem, a network interface card, an antenna, a route (e.g., a Wi-Fi wireless router), and/or the like. Communication component 560 may include one or more communication interfaces, such as a short-range wireless communication interface (e.g., a Wi-Fi interface), a long-range wireless communication interface (e.g., a cellular interface), or the like.

Device 500 may perform one or more processes described herein. For example, a non-transitory computer-readable medium (e.g., memory 530) may store a set of instructions (e.g., one or more instructions, code, software code, program code, and/or the like) for execution by processor 520. Processor 520 may execute the set of instructions to perform one or more processes described herein. In some embodiments, execution of the set of instructions, by one or more processors 520, causes the one or more processors 520 and/or the device 500 to perform one or more processes described herein. In some embodiments, hardwired circuitry may be used instead of or in combination with the instructions to perform one or more processes described herein. Thus, embodiments described herein are not limited to any specific combination of hardware circuitry and software.

In some embodiments, device 500 includes and/or may output a user interface in communication with the processor 520 and operative to provide user input data to the device 500 and to receive and display data, information, and prompts generated by the device 500. The user interface includes at least one input device for receiving user input and providing the user input to the device 500. The user interface may include, for example, a graphical user interface (GUI) including a touchscreen display operative to display data and receive user inputs. The touchscreen display allows the user to interact with presented information, menus, buttons, and other data to receive information from the device 500 and to provide user input to the device 500. Additionally, or alternatively, a keyboard, keypad, microphone, mouse pointer, or other suitable user input device may be included in device 500.

The number and arrangement of components shown in FIG. 5 are provided as an example. Device 500 may include additional components, fewer components, different components, or differently arranged components than those shown in FIG. 5. Additionally, or alternatively, a set of components (e.g., one or more components) of device 500 may perform one or more functions described as being performed by another set of components of device 500.

Figure 6:
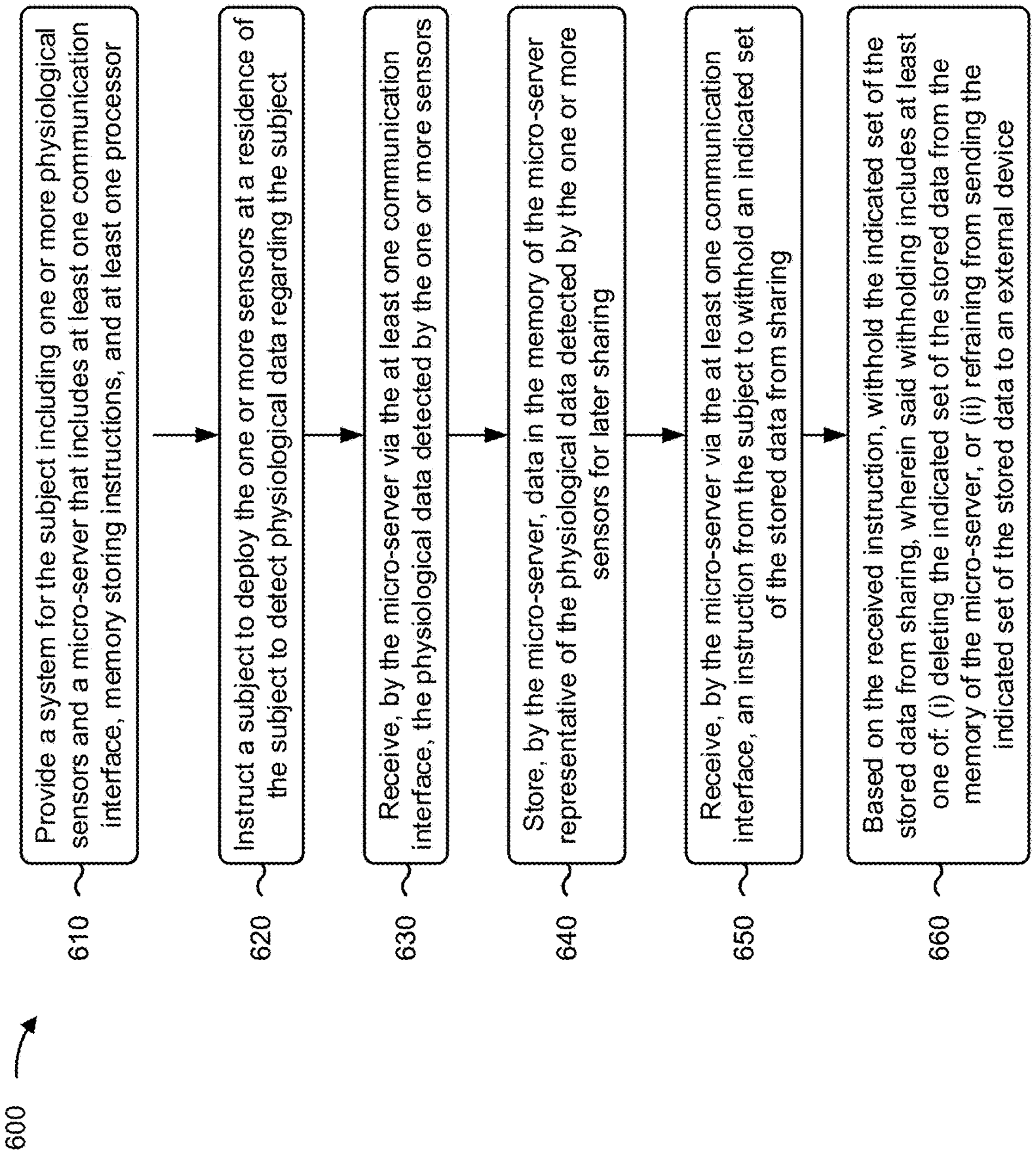
FIGS. 6-8 are flowcharts of example processes associated with a physiological data monitoring system.

FIG. 6 is a flowchart of an example process 600 associated with monitoring physiological data. In some embodiments, one or more process blocks of FIG. 6 may be performed by a micro-server (e.g., micro-server 415). In some embodiments, one or more process blocks of FIG. 6 may be performed by another device or a group of devices separate from or including the micro-server, such as one or more devices described above in connection with FIG. 4. Additionally, or alternatively, one or more process blocks of FIG. 6 may be performed by one or more components of device 500, such as processor 520, memory 530, input component 540, output component 550, and/or communication component 560.

As shown in FIG. 6, process 600 may include providing a system for the subject including one or more physiological sensors and a micro-server that includes at least one communication interface, memory storing instructions, and at least one processor (block 610). As further shown in FIG. 6, process 600 may include instructing the subject to deploy the one or more sensors at a residence of the subject to detect physiological data regarding the subject (block 620). As further shown in FIG. 6, process 600 may include receiving the physiological data detected by the one or more sensors (block 630).

As further shown in FIG. 6, process 600 may include storing data in the memory of the micro-server representative of the physiological data detected by the one or more sensors for later sharing (block 640). As further shown in FIG. 6, process 600 may include receiving an instruction from the subject to withhold an indicated set of the stored data from sharing (block 650). As further shown in FIG. 6, process 600 may include withholding the indicated set of the stored data from sharing, wherein said withholding includes at least one of: (i) deleting the indicated set of the stored data from the memory of the micro-server, or (ii) refraining from sending the indicated set of the stored data to an external device (block 660).

Process 600 may include additional embodiments, such as any single embodiment or any combination of embodiments described below and/or in connection with one or more other processes described elsewhere herein.

In a first embodiment, the one or more physiological sensors include at least one of a video camera, a wrist-mounted actigraphy sensor, a body-mounted actigraphy sensor, a mobile smartphone, a bed vibration sensor, an ambient audio recording device, or a wearable audio recording device.

In a second embodiment, alone or in combination with the first embodiment, process 600 includes retrieving the micro-server from the subject, and downloading the stored data from the memory of the micro-server.

In a third embodiment, alone or in combination with one or more of the first and second embodiments, process 600 includes transmitting, by the micro-server via the at least one communication interface, at least some of the data representative of the physiological data detected by the one or more sensors stored in the memory of the micro-server to the external device, wherein the data transmitted by the micro-server does not include the indicated set of the stored data.

In a fourth embodiment, alone or in combination with one or more of the first through third embodiments, the at least one communication interface includes at least one wireless communication interface.

In a fifth embodiment, alone or in combination with one or more of the first through fourth embodiments, the at least one wireless communication interface includes a short-range wireless communication interface and a long-range wireless communication interface.

In a sixth embodiment, alone or in combination with one or more of the first through fifth embodiments, the external device is at a remote location from the micro-server, and wherein the micro-server receives the physiological data detected by the one or more sensors via the short-range wireless communication interface, and process 600 further includes sending, by the micro-server via the long-range wireless communication interface, data indicative of a state of the micro-server to the external device at the remote location.

In a seventh embodiment, alone or in combination with one or more of the first through sixth embodiments, the short-range wireless communication interface includes a Wi-Fi wireless router, and the long-range wireless communication interface includes a cellular network communication interface.

In an eighth embodiment, alone or in combination with one or more of the first through seventh embodiments, the instruction from the subject to withhold the indicated set of the stored data is received via actuation of one or more physical actuators on a housing of the micro-server.

In a ninth embodiment, alone or in combination with one or more of the first through eighth embodiments, the instruction from the subject to withhold the indicated set of the stored data is received via a wireless signal transmitted by a mobile device or a wearable device of the subject.

In a tenth embodiment, alone or in combination with one or more of the first through ninth embodiments, the instruction from the subject to withhold the indicated set of the stored data is received via a wireless signal transmitted over a cellular network by a server at a remote location.

In an eleventh embodiment, alone or in combination with one or more of the first through tenth embodiments, the instruction from the subject to withhold the indicated set of the stored data identifies at least one of a time period associated with data to be deleted or a physiological sensor associated with data to be deleted.

Although FIG. 6 shows example blocks of process 600, in some embodiments, process 600 may include additional blocks, fewer blocks, different blocks, or differently arranged blocks than those depicted in FIG. 6. Additionally, or alternatively, two or more of the blocks of process 600 may be performed in parallel.

Figure 7:
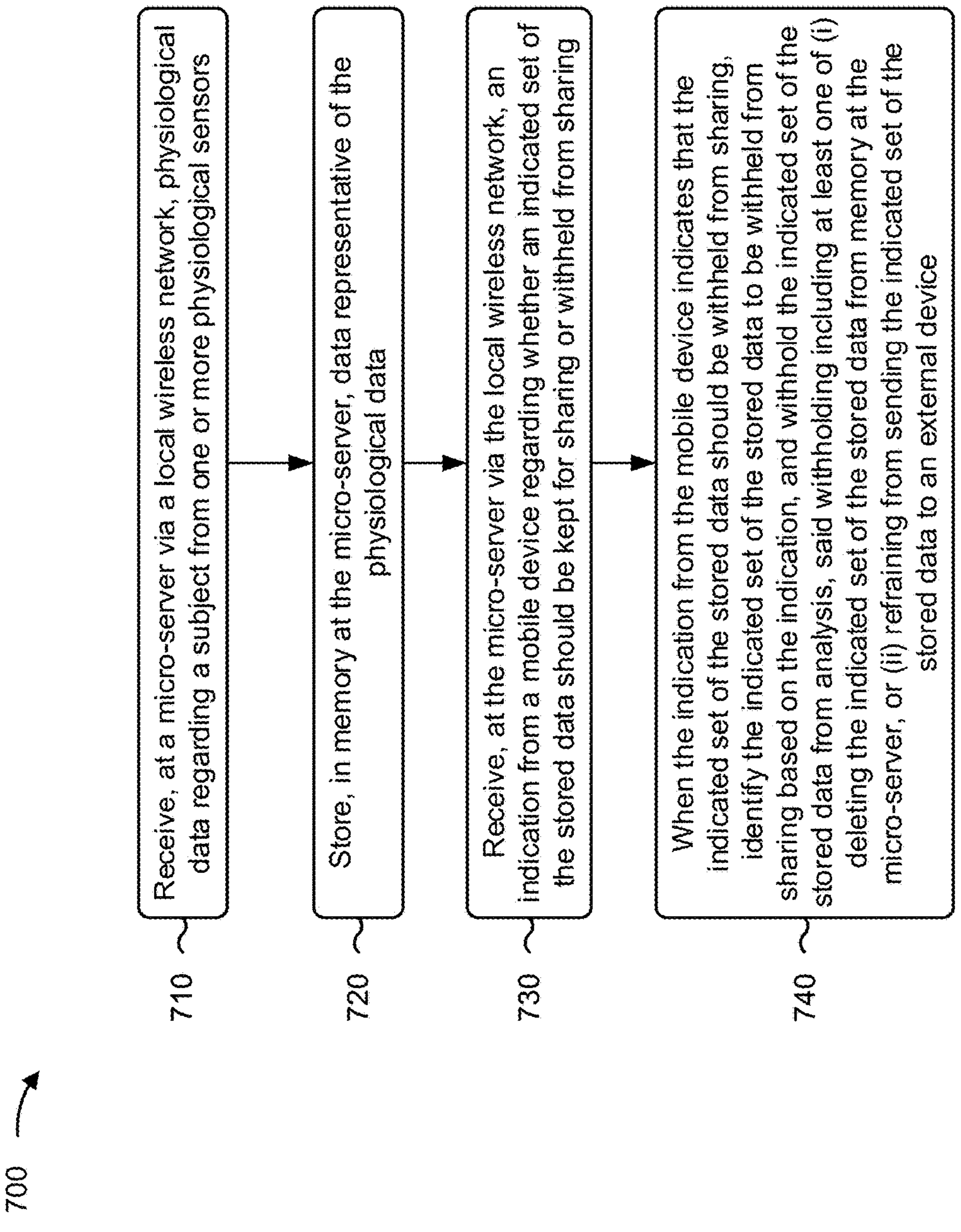

FIG. 7 is a flowchart of an example process 700 associated with monitoring physiological data. In some embodiments, one or more process blocks of FIG. 7 may be performed by a micro-server (e.g., micro-server 415). In some embodiments, one or more process blocks of FIG. 7 may be performed by another device or a group of devices separate from or including the micro-server, such as such as one or more devices described above in connection with FIG. 4. Additionally, or alternatively, one or more process blocks of FIG. 7 may be performed by one or more components of device 500, such as processor 520, memory 530, input component 540, output component 550, and/or communication component 560.

As shown in FIG. 7, process 700 may include receiving, at a micro-server via a local wireless network, physiological data regarding the subject from one or more physiological sensors (block 710). For example, the micro-server may receive, at a micro-server via a local wireless network, physiological data regarding the subject from one or more physiological sensors, as described above.

As further shown in FIG. 7, process 700 may include storing, in memory at the micro-server, data representative of the physiological data (block 720). For example, the micro-server may store, in memory at the micro-server, data representative of the physiological data, as described above.

As further shown in FIG. 7, process 700 may include receiving, at the micro-server via the local wireless network, an indication from a mobile device regarding whether an indicated set of the stored data should be kept for sharing or withheld from sharing (block 730). For example, the micro-server may receive, at the micro-server via the local wireless network, an indication from a mobile device regarding whether an indicated set of the stored data should be kept for sharing or withheld from sharing, as described above.

As further shown in FIG. 7, process 700 may include, when the indication from the mobile device indicates that the indicated set of the stored data should be withheld from sharing, identifying the indicated set of the stored data to be withheld from sharing based on the indication, and withholding the indicated set of the stored data from sharing, said withholding including at least one of (i) deleting the indicated set of the stored data from memory at the micro-server, or (ii) refraining from sending the indicated set of the stored data to an external device (block 740). For example, when the indication from the mobile device indicates that the indicated set of the stored data should be withheld from sharing, the micro-server may identify the indicated set of the stored data to be withheld from sharing based on the indication and withhold the indicated set of the stored data. The withholding including at least one of (i) deleting the indicated set of the stored data from memory at the micro-server, or (ii) refraining from sending the indicated set of the stored data to an external device, as described above.

Process 700 may include additional embodiments, such as any single embodiment or any combination of embodiments described below and/or in connection with one or more other processes described elsewhere herein.

In a first embodiment, process 700 includes sending, from the micro-server via the local wireless network, a request to the mobile device of the subject to confirm whether the indicated set of the stored data should be kept for sharing or withheld from sharing, and receiving the indication from the mobile device regarding whether the indicated set of the stored data should be kept for sharing or withheld from sharing based on sending the request.

In a second embodiment, alone or in combination with the first embodiment, the external device is a remote server, and process 700 further includes sending the stored data from the micro-server to the remote server via a cellular network separate from the local wireless network only when the indication from the mobile device indicates the indicated set of the stored data should be kept for sharing.

In a third embodiment, alone or in combination with one or more of the first and second embodiments, the external device is a remote server, and process 700 further includes sending at least one status update from the micro-server to the remote server via a cellular network separate from the local wireless network, the at least one status update including data representative at least one of (i) a battery charge of at least one of sensors or (ii) a connection status between at least one of the sensors and the micro-server.

In a fourth embodiment, alone or in combination with one or more of the first through third embodiments, the one or more physiological sensors include at least one of a video camera, a wrist-mounted actigraphy sensor, a body-mounted actigraphy sensor, a mobile smartphone, a bed vibration sensor, or an audio recording device.

In a fifth embodiment, alone or in combination with one or more of the first through fourth embodiments, the indicated set of the stored data is identified based on information, included in the indication, that indicates at least one of a time period associated with data to be deleted or a physiological sensor associated with data to be deleted.

Although FIG. 7 shows example blocks of process 700, in some embodiments, process 700 may include additional blocks, fewer blocks, different blocks, or differently arranged blocks than those depicted in FIG. 7. Additionally, or alternatively, two or more of the blocks of process 700 may be performed in parallel.

Figure 8:
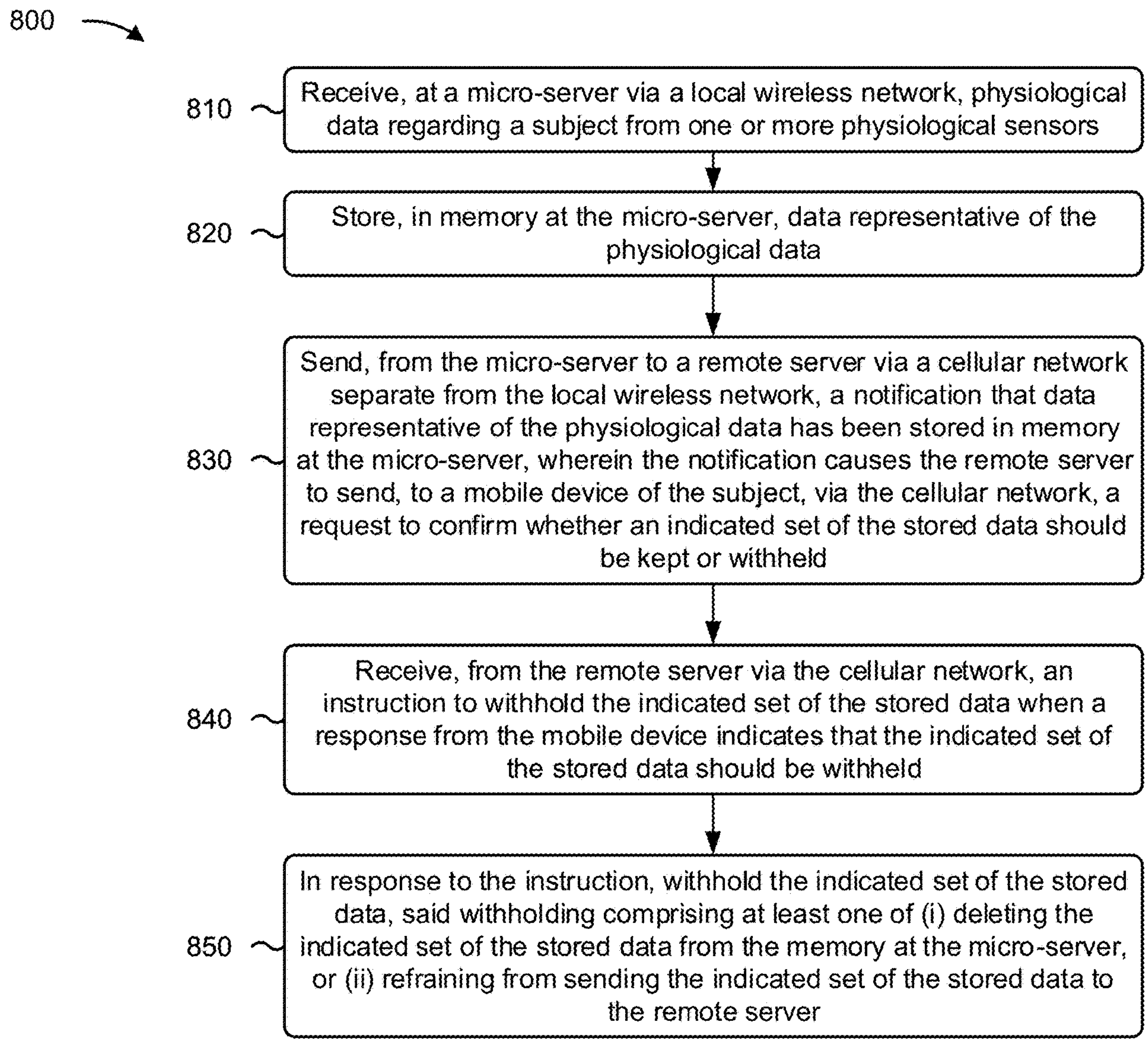

FIG. 8 is a flowchart of an example process 800 associated with monitoring physiological data. In some embodiments, one or more process blocks of FIG. 8 may be performed by a micro-server (e.g., micro-server 415). In some embodiments, one or more process blocks of FIG. 8 may be performed by another device or a group of devices separate from or including the micro-server, such as such as one or more devices described above in connection with FIG. 4. Additionally, or alternatively, one or more process blocks of FIG. 8 may be performed by one or more components of device 500, such as processor 520, memory 530, input component 540, output component 550, and/or communication component 560.

As shown in FIG. 8, process 800 may include receiving, at a micro-server via a local wireless network, physiological data regarding the subject from one or more physiological sensors (block 810). For example, the micro-server may receive, via a local wireless network, physiological data regarding the subject from one or more physiological sensors, as described above.

As further shown in FIG. 8, process 800 may include storing, in memory at the micro-server, data representative of the physiological data (block 820). For example, the micro-server may store, in memory at the micro-server, data representative of the physiological data, as described above.

As further shown in FIG. 8, process 800 may include sending, from the micro-server to a remote server via a cellular network separate from the local wireless network, a notification that data representative of the physiological data has been stored in memory at the micro-server, wherein the notification causes the remote server to send, to a mobile device of the subject, via the cellular network, a request to confirm whether an indicated set of the stored data should be kept or withheld (block 830). For example, the micro-server may send, from the micro-server to a remote server via a cellular network separate from the local wireless network, a notification that data representative of the physiological data has been stored in memory at the micro-server, wherein the notification causes the remote server to send, to a mobile device of the subject, via the cellular network, a request to confirm whether an indicated set of the stored data should be kept or withheld, as described above.

As further shown in FIG. 8, process 800 may include receiving, from the remote server via the cellular network, an instruction to withhold the indicated set of the stored data when a response from the mobile device indicates that the indicated set of the stored data should be withheld (block 840). For example, the micro-server may receive, from the remote server via the cellular network, an instruction to withhold the indicated set of the stored data when a response from the mobile device indicates that the indicated set of the stored data should be withheld, as described above.

As further shown in FIG. 8, process 800 may include, in response to the instruction, withholding the indicated set of the stored data, said withholding including at least one of (i) deleting the indicated set of the stored data from the memory at the micro-server, or (ii) refraining from sending the indicated set of the stored data to the remote server (block 850). For example, in response to the instruction, the micro-server may withhold the indicated set of the stored data, as described above. The withholding may include at least one of (i) deleting the indicated set of the stored data from the memory at the micro-server, or (ii) refraining from sending the indicated set of the stored data to the remote server, as described above.

Process 800 may include additional embodiments, such as any single embodiment or any combination of embodiments described below and/or in connection with one or more other processes described elsewhere herein.

In a first embodiment, process 800 includes sending the indicated set of the stored data from the micro-server to the remote server via the cellular network only when the response from the mobile device indicates that the indicated set of the stored data should be kept.

In a second embodiment, alone or in combination with the first embodiment, process 800 includes sending at least one status update from the micro-server to the remote server via the cellular network, the at least one status update including data representative at least one of (i) a battery charge of at least one of sensors, or (ii) a connection status between at least one of the sensors and the micro-server.

In a third embodiment, alone or in combination with one or more of the first and second embodiments, the one or more physiological sensors include at least one of a video camera, a wrist-mounted actigraphy sensor, a mobile smartphone, and a bed vibration sensor.

Although FIG. 8 shows example blocks of process 800, in some embodiments, process 800 may include additional blocks, fewer blocks, different blocks, or differently arranged blocks than those depicted in FIG. 8. Additionally, or alternatively, two or more of the blocks of process 800 may be performed in parallel.

The terms "first", "second", "third", and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method for facilitating a subject to record physiological data regarding him- or herself and to allow the subject to withhold a subset of the recorded physiological data from sharing, the method comprising:

providing a system for the subject comprising:

a plurality of types of physiological sensors, the physiological sensors comprising a video camera, and a micro-server comprising at least one communication interface, memory storing instructions, and at least one processor;

instructing the subject to deploy the sensors at a residence of the subject to detect physiological data regarding the subject, the physiological data comprising video recorded by the video camera capturing movement of the subject;

receiving, by the micro-server from a mobile device of the subject, an instruction to initiate data gathering;

transmitting, by the micro-server in response to the received instruction, instructions to the physiological sensors to begin gathering data;

receiving, by the micro-server via the at least one communication interface, the physiological data detected by the sensors;

storing, by the micro-server, data in the memory of the micro-server representative of the physiological data detected by the sensors for later sharing;

after receiving the physiological data and storing the data representative of the physiological data, prompting the subject regarding whether the stored data should be withheld from sharing;

receiving in response to the prompt, by the micro-server via the at least one communication interface, an instruction from the subject to withhold an indicated set of the stored data from sharing, the instruction comprising an instruction to withhold data received from an indicated type of physiological sensor; and based on the received instruction, withholding the indicated set of the stored data from sharing, wherein said withholding comprises at least one of: (i) deleting the indicated set of the stored data from the memory of the micro-server, or (ii) refraining from sending the indicated set of the stored data to an external device.

2. The method of claim 1, wherein the physiological sensors further comprise at least one of a wrist-mounted actigraphy sensor, a body-mounted actigraphy sensor, a mobile smartphone, a bed vibration sensor, an ambient audio recording device, or a wearable audio recording device.

3. The method of claim 1, further comprising:

retrieving the micro-server from the subject; and downloading the stored data from the memory of the micro-server.

4. The method of claim 1, further comprising transmitting, by the micro-server via the at least one communication interface, at least some of the data representative of the physiological data detected by the sensors stored in the memory of the micro-server to the external device, wherein the data transmitted by the micro-server does not include the indicated set of the stored data.

5. The method of claim 1, wherein the at least one communication interface comprises at least one wireless communication interface.

6. The method of claim 5, wherein the at least one wireless communication interface comprises a short-range wireless communication interface and a long-range wireless communication interface.

7. The method of claim 6, wherein the external device is at a remote location from the micro-server, and wherein the micro-server receives the physiological data detected by the sensors via the short-range wireless communication interface, the method further comprising sending, by the micro-server via the long-range wireless communication interface, data indicative of a state of the micro-server to the external device at the remote location.

8. The method of claim 6, wherein the short-range wireless communication interface comprises a Wi-Fi wireless router, and the long-range wireless communication interface comprises a cellular network communication interface.

9. The method of claim 1, wherein the instruction from the subject to withhold the indicated set of the stored data is received via actuation of one or more physical actuators on a housing of the micro-server.

10. The method of claim 1, wherein the instruction from the subject to withhold the indicated set of the stored data is received via a wireless signal transmitted by a mobile device or a wearable device of the subject.

11. The method of claim 1, wherein the instruction from the subject to withhold the indicated set of the stored data is received via a wireless signal transmitted over a cellular network by a server at a remote location.

12. The method of claim 1, wherein the instruction from the subject to withhold the indicated set of the stored data identifies at least one of a time period associated with data to be deleted or a physiological sensor associated with data to be deleted.

13. A method for facilitating a subject to record physiological data regarding the subject and to allow the subject to withhold a set of the recorded physiological data from sharing, the method comprising:

receiving, at a micro-server from a mobile device of the subject, an instruction to initiate data gathering;

transmitting, by the micro-server in response to the received instruction, instructions to a plurality of types of physiological sensors to begin gathering data, wherein the physiological sensors comprise a video camera;

receiving, at the micro-server via a local wireless network, physiological data regarding the subject from the plurality of types of physiological sensors, wherein the physiological data comprises video recorded by the video camera capturing movement of the subject;

storing, in memory at the micro-server, data representative of the physiological data;

after receiving the physiological data and storing the data representative of the physiological data, prompting the subject regarding whether the stored data should be withheld from sharing;

receiving in response to the prompt, at the micro-server via the local wireless network, an indication from a mobile device; and when the indication from the mobile device indicates that an indicated set of the stored data received from an indicated type of physiological sensor should be withheld from sharing:

identifying the indicated set of the stored data to be withheld from sharing based at least in part on the indicated type of physiological sensor, and withholding the indicated set of the stored data from sharing, said withholding comprising at least one of (i) deleting the indicated set of the stored data from memory at the micro-server, or (ii) refraining from sending the indicated set of the stored data to an external device.

14. The method of claim 13, further comprising:

sending, from the micro-server via the local wireless network, a request to the mobile device of the subject to confirm whether the indicated set of the stored data should be kept for sharing or withheld from sharing; and receiving the indication from the mobile device regarding whether the indicated set of the stored data should be kept for sharing or withheld from sharing based on sending the request.

15. The method of claim 13, wherein the external device is a remote server, the method further comprising sending the stored data from the micro-server to the remote server via a cellular network separate from the local wireless network only when the indication from the mobile device indicates the indicated set of the stored data should be kept for sharing.

16. The method of claim 13, wherein the external device is a remote server, the method further comprising sending at least one status update from the micro-server to the remote server via a cellular network separate from the local wireless network, the at least one status update including data representative at least one of (i) a battery charge of at least one of sensors or (ii) a connection status between at least one of the sensors and the micro-server.

17. The method of claim 13, wherein the physiological sensors further comprise at least one of a wrist-mounted actigraphy sensor, a body-mounted actigraphy sensor, a mobile smartphone, a bed vibration sensor, or an audio recording device.

18. The method of claim 13, wherein the indicated set of the stored data is identified based on information, included in the indication, that indicates at least one of a time period associated with data to be deleted or a physiological sensor associated with data to be deleted.

19. A method for facilitating a subject to record physiological data regarding the subject and to allow the subject to withhold a set of the recorded physiological data, the method comprising:

receiving, at a micro-server from a mobile device of the subject, an instruction to initiate data gathering;

transmitting, by the micro-server in response to the received instruction, instructions to a plurality of types of physiological sensors to begin gathering data, wherein the physiological sensors comprises a video camera;

receiving, at the micro-server via a local wireless network, physiological data regarding the subject from the plurality of types of physiological sensors, wherein the physiological data comprises video recorded by the video camera capturing movement of the subject;

storing, in memory at the micro-server, data representative of the physiological data;

sending, from the micro-server to a remote server via a cellular network separate from the local wireless network, a notification that data representative of the physiological data has been stored in memory at the micro-server, wherein the notification causes the remote server to send, to a mobile device of the subject, via the cellular network, a request;

receiving, from the remote server via the cellular network, an instruction to withhold an indicated set of the stored data received from an indicated type of physiological sensor when a response from the mobile device indicates that the indicated set of the stored data should be withheld; and in response to the instruction, withholding the indicated set of the stored data based at least in part on the indicated type of physiological sensor, said withholding comprising at least one of (i) deleting the indicated set of the stored data from the memory at the micro-server, or (ii) refraining from sending the indicated set of the stored data to the remote server.

20. The method of claim 19, further comprising sending the indicated set of the stored data from the micro-server to the remote server via the cellular network only when the response from the mobile device indicates that the indicated set of the stored data should be kept.

21. The method of claim 19, further comprising sending at least one status update from the micro-server to the remote server via the cellular network, the at least one status update including data representative at least one of (i) a battery charge of at least one of the sensors, or (ii) a connection status between at least one of the sensors and the micro-server.

22. The method of claim 19, wherein the physiological sensors further comprise a wrist-mounted actigraphy sensor, a mobile smartphone, and a bed vibration sensor.

23. A micro-server, comprising:

one or more memories; and one or more processors, communicatively coupled to one or more the memories, configured to:

receive, from a mobile device of a subject, an instruction to initiate data gathering;

transmit, by the micro-server in response to the received instruction, instructions to a plurality of types of physiological sensors to begin gathering data, wherein the physiological sensors comprise a video camera;

receive, at the micro-server via a local wireless network, physiological data regarding the subject from the plurality of types of physiological sensors, wherein the physiological data comprises video recorded by the video camera capturing movement of the subject;

store, in memory at the micro-server, data representative of the physiological data;

send, from the micro-server to a remote server via a cellular network separate from the local wireless network, a notification that data representative of the physiological data has been stored in memory at the micro-server, wherein the notification causes the remote server to send, to a mobile device of the subject, via the cellular network, a request;

receive, from the remote server via the cellular network, an instruction to withhold an indicated set of the stored data received from an indicated type of physiological sensor when a response from the mobile device indicates that the indicated set of the stored data should be withheld; and in response to the instruction, withhold the indicated set of the stored data based at least in part on the indicated type of physiological sensor, said withholding comprising at least one of (i) deleting the indicated set of the stored data from the memory at the micro-server, or (ii) refraining from sending the indicated set of the stored data to the remote server.

* * * * *